(12) United States Patent
Kaula et al.

(10) Patent No.: US 10,391,321 B2
(45) Date of Patent: *Aug. 27, 2019

(54) SYSTEMS, METHODS, AND DEVICES FOR EVALUATING LEAD PLACEMENT BASED ON GENERATED VISUAL REPRESENTATIONS OF SACRUM AND LEAD

(71) Applicant: Nuvectra Corporation, Plano, TX (US)

(72) Inventors: Norbert Kaula, Arvada, CO (US);
Yohannes Iyassu, Denver, CO (US);
Steven Siegel, North Oaks, MN (US)

(73) Assignee: NUVECTRA CORPORATION, Plano, TX (US)

( * ) Notice: Subject to any disclaimer, the term of this patent is extended or adjusted under 35 U.S.C. 154(b) by 37 days.

This patent is subject to a terminal disclaimer.

(21) Appl. No.: 15/688,454

(22) Filed: Aug. 28, 2017

(65) Prior Publication Data

US 2018/0008834 A1    Jan. 11, 2018

Related U.S. Application Data

(63) Continuation of application No. 15/174,318, filed on Jun. 6, 2016, now Pat. No. 9,750,946.
(Continued)

(51) Int. Cl.
*A61N 1/00* (2006.01)
*A61N 1/372* (2006.01)
(Continued)

(52) U.S. Cl.
CPC ..... *A61N 1/37247* (2013.01); *A61N 1/36057* (2013.01); *A61N 1/36071* (2013.01);
(Continued)

(58) Field of Classification Search
CPC ............ A61N 1/37247; A61N 1/36057; A61N 1/36071; A61N 1/36142; A61N 1/36135;
(Continued)

(56) References Cited

U.S. PATENT DOCUMENTS

| 4,245,641 A | 1/1981 | Mann et al. |
| 4,503,863 A | 3/1985 | Katims |

(Continued)

FOREIGN PATENT DOCUMENTS

| EP | 1 048 317 | 11/2000 |
| EP | 2 567 729 | 3/2013 |

(Continued)

OTHER PUBLICATIONS

European Patent Office, "European Search Report" for Application No. 16172698.9, dated Sep. 8, 2016, 8 pages.
(Continued)

*Primary Examiner* — Scott M. Getzow
(74) *Attorney, Agent, or Firm* — Haynes and Boone, LLP; Eric Li

(57) ABSTRACT

A method of evaluating an implantation of a lead is disclosed. Via a graphical user interface of an electronic device, a visual representation of a sacrum of the patient and a lead that is implanted in the sacrum is displayed. The lead includes a plurality of electrode contacts. An evaluation is made as to how well the lead has been implanted in the sacrum based on the visual representation of the sacrum and the lead. The evaluating comprises: determining whether the lead is inserted in a predetermined region of the sacrum, determining how far a predetermined one of the electrode contacts is located from an edge of the sacrum, and determining a degree of curvature of the lead.

20 Claims, 22 Drawing Sheets

Related U.S. Application Data

(60) Provisional application No. 62/181,827, filed on Jun. 19, 2015, provisional application No. 62/173,118, filed on Jun. 9, 2015.

(51) Int. Cl.
*A61N 1/36* (2006.01)
*A61N 1/05* (2006.01)

(52) U.S. Cl.
CPC ........ *A61N 1/0551* (2013.01); *A61N 1/36007* (2013.01); *A61N 1/36107* (2013.01); *A61N 1/36132* (2013.01); *A61N 1/36135* (2013.01); *A61N 1/36142* (2013.01)

(58) Field of Classification Search
CPC ............ A61N 1/36132; A61N 1/36007; A61N 1/0551; A61N 1/36107
See application file for complete search history.

(56) References Cited

U.S. PATENT DOCUMENTS

| | | | |
|---|---|---|---|
| 5,725,560 | A | 3/1998 | Brink |
| 6,275,735 | B1 | 8/2001 | Jarding et al. |
| 6,505,074 | B2 | 1/2003 | Boveja et al. |
| 7,174,213 | B2 | 2/2007 | Pless |
| 7,601,116 | B2 | 10/2009 | Fischell et al. |
| 7,881,783 | B2 | 2/2011 | Bonde et al. |
| 8,060,208 | B2 | 11/2011 | Kilgore et al. |
| 8,095,216 | B1 | 1/2012 | Moulder et al. |
| 8,112,154 | B2 | 2/2012 | Rezai et al. |
| 8,260,412 | B2 | 9/2012 | Krause et al. |
| 8,688,217 | B2 | 4/2014 | Aghassian et al. |
| 8,751,016 | B2 | 6/2014 | Schleicher et al. |
| 8,761,897 | B2 | 6/2014 | Kaula et al. |
| 8,805,515 | B2 | 8/2014 | York et al. |
| 9,014,813 | B2 | 4/2015 | Foutz et al. |
| 9,144,680 | B2 | 9/2015 | Kaula et al. |
| 2004/0098065 | A1 | 5/2004 | Hagglof et al. |
| 2006/0122660 | A1 | 6/2006 | Boveja et al. |
| 2008/0039866 | A1* | 2/2008 | Stetz ............... A61B 90/11 606/129 |
| 2010/0280575 | A1 | 11/2010 | Carbunaru et al. |
| 2011/0307032 | A1 | 12/2011 | Goetz et al. |
| 2012/0101326 | A1 | 4/2012 | Simon et al. |
| 2013/0296966 | A1 | 11/2013 | Wongsarnpigoon et al. |
| 2013/0304152 | A1 | 11/2013 | Bradley et al. |
| 2014/0046398 | A1 | 2/2014 | Sachs et al. |
| 2014/0067013 | A1 | 3/2014 | Kaula et al. |
| 2014/0067019 | A1 | 3/2014 | Kothandaraman et al. |
| 2014/0067020 | A1 | 3/2014 | Kaula et al. |
| 2014/0068758 | A1 | 3/2014 | Kaula et al. |
| 2014/0180361 | A1 | 6/2014 | Burdick et al. |
| 2014/0222102 | A1 | 8/2014 | Lemus et al. |
| 2014/0249599 | A1 | 9/2014 | Kaula et al. |
| 2015/0119958 | A1 | 4/2015 | Li et al. |
| 2015/0134027 | A1 | 5/2015 | Kaula et al. |
| 2015/0134028 | A1 | 5/2015 | Kaula et al. |
| 2016/0022996 | A1 | 1/2016 | Kaula et al. |
| 2016/0045747 | A1* | 2/2016 | Jiang ............. A61N 1/37241 607/40 |
| 2016/0121126 | A1 | 5/2016 | Marnfeldt |

FOREIGN PATENT DOCUMENTS

| | | |
|---|---|---|
| WO | WO 2006/107848 | 10/2006 |
| WO | WO 2009/097224 | 8/2009 |
| WO | WO 2011/156288 | 12/2011 |

OTHER PUBLICATIONS

European Patent Office, "European Search Report" for Application No. 16172706.0, dated Oct. 10, 2016, 7 pages.
European Patent Office, "European Search Report" for Application No. 16172702.9, dated Oct. 26, 2016, 8 pages.
European Patent Office, "European Search Report" for Application No. 16173541.0, dated Nov. 3, 2016, 6 pages.
European Patent Office, "Communication Pursuant to Article 94(#) EPC" for Application No. 16172702.9, dated Nov. 15, 2018.

* cited by examiner

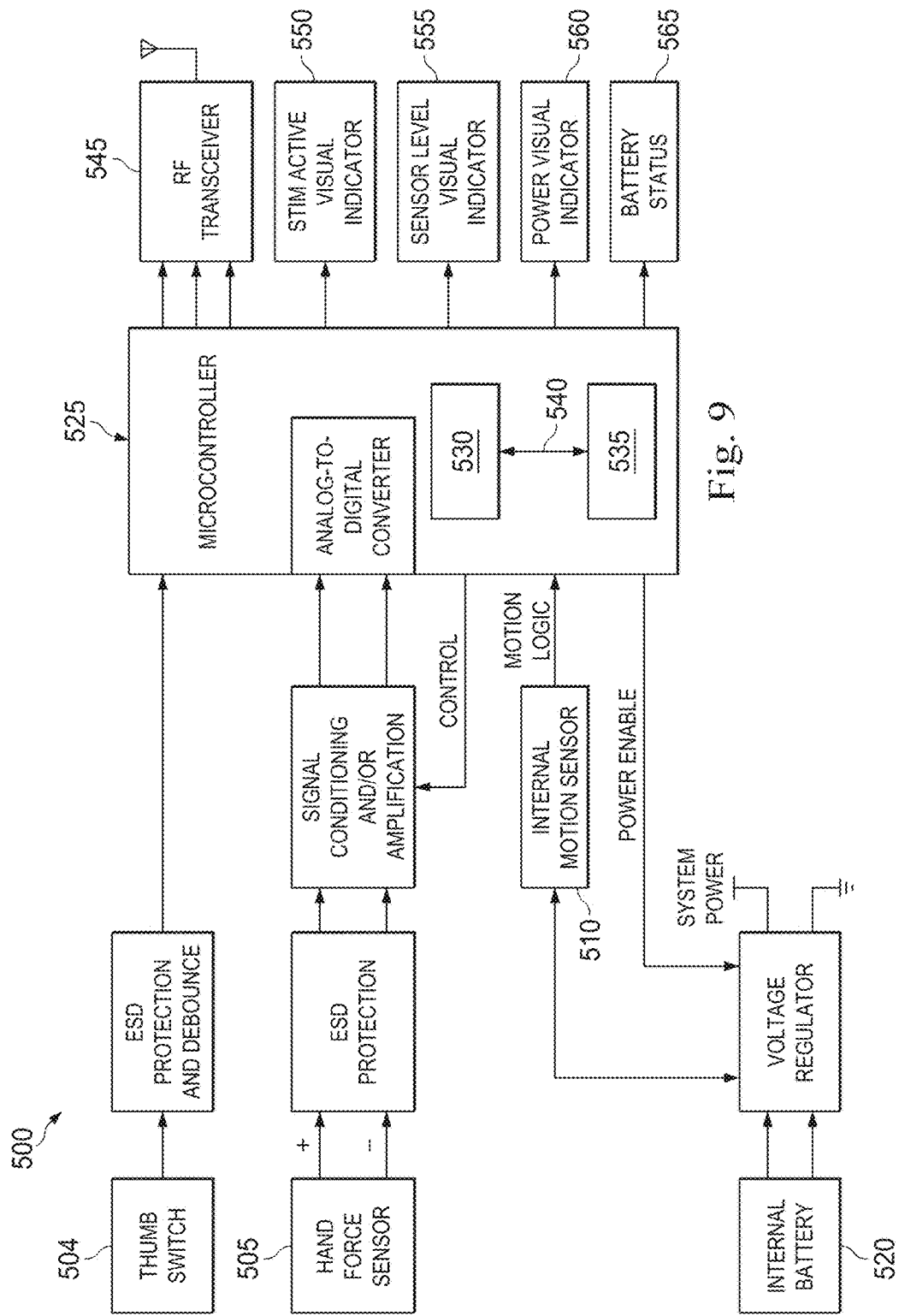

SYSTEMS, METHODS, AND DEVICES FOR EVALUATING LEAD PLACEMENT BASED ON GENERATED VISUAL REPRESENTATIONS OF SACRUM AND LEAD

PRIORITY DATA

The present application is a continuation of U.S. patent application Ser. No. 15/174,318, filed Jun. 6, 2016, entitled "Systems, Methods, and Devices for Evaluating Lead Placement based on Generated Visual Representations of Sacrum and Lead," now U.S. Pat. No. 9,750,946 which is a utility application of provisional U.S. Patent Application No. 62/173,118, filed on Jun. 9, 2015, entitled "Advanced Methods and Apparatuses for Performing Pelvic Nerve Stimulation," and a utility application of provisional U.S. Patent Application No. 62/181,827, filed on Jun. 19, 2015, entitled "Advanced Methods and Apparatuses for Performing Pelvic Nerve Stimulation," the disclosures of each which are hereby incorporated by reference in their respective entireties.

BACKGROUND

The invention relates to a stimulation system, such as a pelvic nerve or sacral nerve stimulation system, having a tool for programming an electrical stimulation generator, such as an implantable pulse generator (IPG), of the system.

A sacral nerve stimulator is a device used to provide electrical stimulation to the pelvic region of a patient, for example the sacral nerve or the pudendal nerve, in order to treat problems such as incontinence. The stimulator includes an implanted or external pulse generator and an implanted stimulation lead having one or more electrodes at a distal location thereof. The pulse generator provides the stimulation through the electrodes via a body portion and connector of the lead. Stimulation programming in general refers to the configuring of stimulation electrodes and stimulation parameters to treat the patient using one or more implanted leads and its attached IPG. For example, the programming is typically achieved by selecting individual electrodes and adjusting the stimulation parameters, such as the shape of the stimulation waveform, amplitude of current in mA (or amplitude of voltage in V), pulse width in microseconds, frequency in Hz, and anodic or cathodic stimulation.

Despite recent advances in medical technology, existing pelvic or sacral nerve stimulation methods, systems, and devices still have various shortcomings. For example, one problem faced by existing pelvic or sacral nerve stimulation systems and methods is that they lack a reliable way to indicate how well the lead has been placed or implanted inside the patient. The correct implantation of the lead is crucial, as a correctly-implanted lead can produce stimulation therapy that stimulates the patient effectively, whereas it may be difficult for an incorrectly implanted lead (or even a lead that is not implanted optimally) to produce the stimulation therapy to treat the patient effectively. Often times, even doctors (who may lack experience in this particular field) cannot accurately evaluate how well the lead has been implanted.

Therefore, although existing systems and methods for performing sacral nerve stimulation are generally adequate for their intended purposes, they have not been entirely satisfactory in all respects.

SUMMARY

One aspect of the present disclosure involves an electronic device. The electronic device includes a graphical user interface configured to receive an input from a user and display an output to the user. The electronic device includes an electronic memory storage configured to store programming instructions. The electronic device includes one or more processors configured to execute the programming instructions to perform the following steps: displaying, via the graphical user interface, a visual representation of a sacrum of the patient and a lead that is implanted in the sacrum, the lead including a plurality of electrode contacts; and evaluating how well the lead has been implanted in the sacrum based on the visual representation of the sacrum and the lead, wherein the evaluating comprises: determining whether the lead is inserted in a predetermined region of the sacrum; determining how far a predetermined one of the electrode contacts is located from an edge of the sacrum; and determining a degree of curvature of the lead.

Another aspect of the present disclosure involves a medical system. The medical system includes: a pulse generator configured to generate electrical stimulation pulses as a part of an electrical stimulation therapy for a patient; an implantable lead configured to deliver the electrical stimulation pulses to the patient; and a portable electronic programmer that is telecomniunicatively coupled to the pulse generator through a communications link, wherein the portable electronic device is configured to perform the following steps: displaying, via a graphical user interface of an electronic device, a visual representation of a sacrum of the patient and a lead that is implanted in the sacrum, the lead including a plurality of electrode contacts; and evaluating how well the lead has been implanted in the sacrum based on the visual representation of the sacrum and the lead, wherein the evaluating comprises: determining whether the lead is inserted in a predetermined region of the sacrum; determining how far a predetermined one of the electrode contacts is located from an edge of the sacrum; and determining a degree of curvature of the lead.

Yet another aspect of the present disclosure involves a method of evaluating a placement of a lead configured to deliver an electrical stimulation therapy for a patient. The method comprises: displaying, via a graphical user interface of an electronic device, a visual representation of a sacrum of the patient and a lead that is implanted in the sacrum, the lead including a plurality of electrode contacts; and evaluating, via one or more hardware processors of the electronic device, how well the lead has been implanted in the sacrum based on the visual representation of the sacrum and the lead, wherein the evaluating comprises: determining whether the lead is inserted in a predetermined region of the sacrum; determining how far a predetermined one of the electrode contacts is located from an edge of the sacrum; and determining a degree of curvature of the lead.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIG. 9 is a diagrammatic block diagram of a patient feedback device according to an embodiment of the present disclosure.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
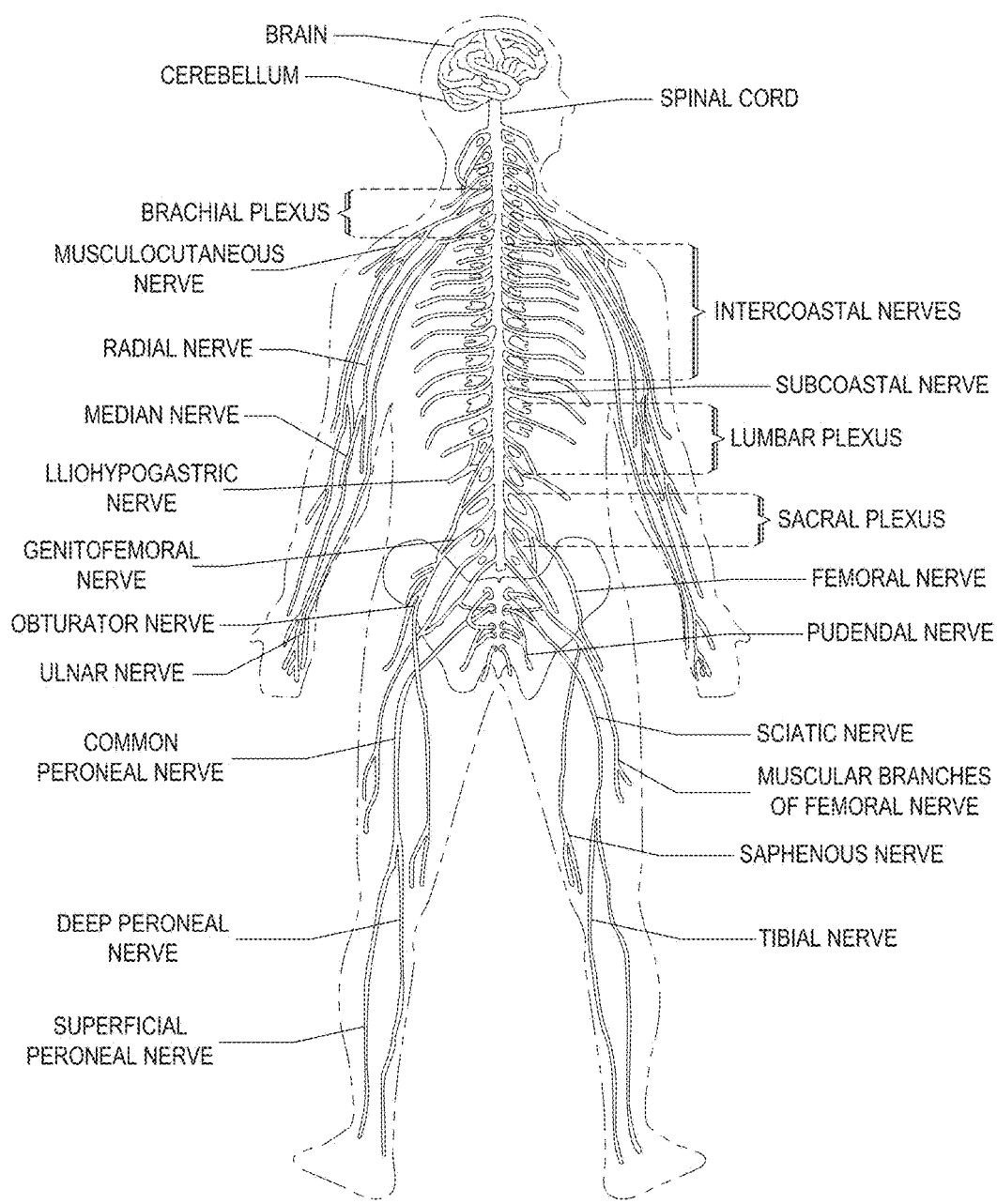
FIG. 1 is stylized overview of the human nervous system.

The human nervous system includes a complex network of neurological structures that extend throughout the body. As shown in FIG. 1, the brain interconnects with the spinal cord which branches into the brachial plexus near the shoulders and the lumbar plexus and sacral plexus in the lower back. The limb peripheral nerves of the arms extend distally from the brachial plexus down each arm. Similarly, the limb peripheral nerves of the legs extend distally from the lumbar plexus and sacral plexus. A number of the larger limb peripheral nerves are identified in FIG. 1. As discussed further below, certain aspects of the present invention are particularly well suited to stimulation of the pudendal nerves and the sacral nerves, including those identified in FIG. 1.

Figure 2B:
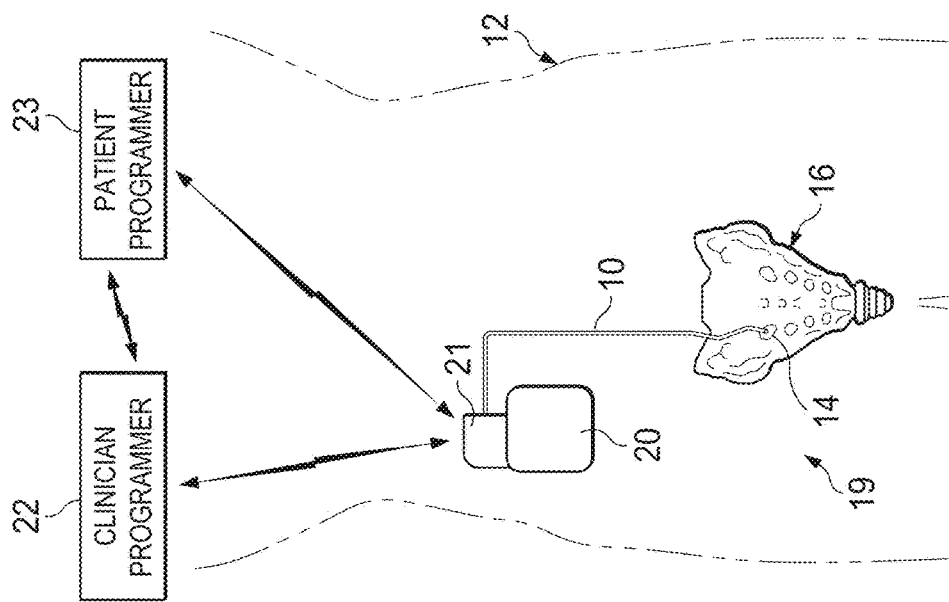
FIG. 2B is a simplified diagram illustrating an implantable neurostimulation system for stimulating nerves according to various embodiments of the present disclosure.
Figure 2A:
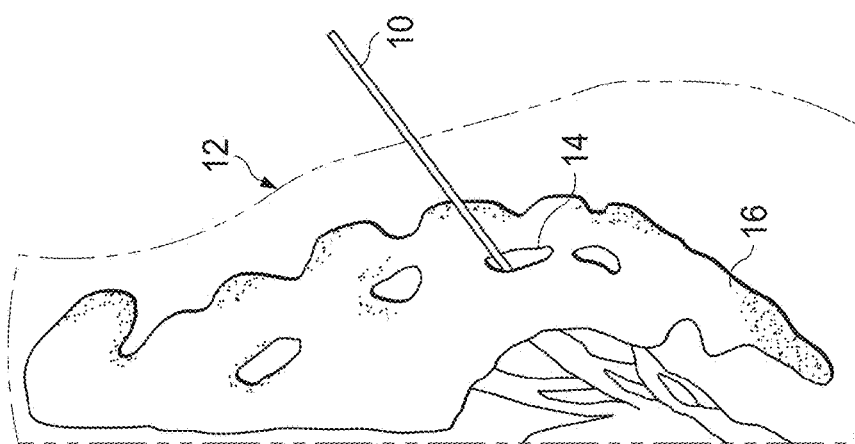
FIG. 2A is a diagram illustrating an example sacral implantation of a neurostimulation lead according to various embodiments of the present disclosure.

FIG. 2A is a simplified diagram illustrating implantation of a neurostimulation lead 10. In the example of FIG. 2A, lead 10 is inserted into body 12 of a patient, and implanted posterior to one of dorsal foramen 14 of sacrum 16. However, lead 10 alternatively may be positioned to stimulate pudendal nerves, perineal nerves, sacral spinal nerves, or other areas of the nervous system. Lead 10 may be implanted via a needle and stylet for minimal invasiveness. Positioning of lead 10 may be aided by imaging techniques, such as fluoroscopy. In some embodiments, a plurality of stimulation leads may be provided.

FIG. 2B is a diagram illustrating an implantable neurostimulation system 19 for stimulating a nerve, such as a sacral nerve, via the lead 10. Neurostimulation system 19 delivers neurostimulation to the sacral nerves or other regions of the nervous system known to treat problems including, but are not limited to: pelvic floor disorders, urinary control disorders, fecal control disorders, interstitial cystitis, sexual dysfunction, and pelvic pain. As shown in FIG. 2B, system 19 includes lead 10 and an implantable pulse generator (IPG). In addition, a proximal end of stimulation lead 10 may be coupled to a connector block 21 associated with the neurostimulator 20.

In some embodiments, the neurostimulator 20 includes an implantable pulse generator (IPG), and delivers neurostimulation therapy to patient 12 in the form of electrical pulses generated by the IPG. In the example of FIG. 2B, the neurostimulator 20 is implanted in the upper left buttock of patient 12, but it is understood that the neurostimulator 20 be implanted at other locations in alternative embodiments.

The lead 10 carries one or more of stimulation electrodes, e.g., 1 to 8 electrodes, to permit delivery of electrical stimulation to the target nerve, such as the sacral nerve. For example, the implantable neurostimulation system 19 may stimulate organs involved in urinary, fecal or sexual function via C-fibers or sacral nerves at the second, third, and fourth sacral nerve positions, commonly referred to as S2, S3, and S4, respectively. In some embodiments, the neurostimulator 20 may be coupled to two or more leads deployed at different positions, e.g., relative to the spinal cord or sacral nerves.

The implantable neurostimulation system 19 also may include a clinician programmer 22 and a patient programmer 23. The clinician programmer 22 may be a handheld computing device that permits a clinician to program neurostimulation therapy for patient 12, e.g., using input keys and a display. For example, using clinician programmer 22, the clinician may specify neurostimulation parameters for use in delivery of neurostimulation therapy. The clinician programmer 22 supports radio frequency telemetry with neurostimulator 20 to download neurostimulation parameters and, optionally, upload operational or physiological data stored by the neurostimulator. In this manner, the clinician may periodically interrogate neurostimulator 20 to evaluate efficacy and, if necessary, modifies the stimulation parameters.

Similar to clinician programmer 22, patient programmer 23 may be a handheld computing device. The patient programmer 23 may also include a display and input keys to allow patient 12 to interact with patient programmer 23 and implantable neurostimulator 20. In this manner, the patient programmer 23 provides the patient 12 with an interface for control of neurostimulation therapy by neurostimulator 20. For example, the patient 12 may use patient programmer 23 to start, stop or adjust neurostimulation therapy. In particular, the patient programmer 23 may permit the patient 12 to adjust stimulation parameters such as duration, amplitude, pulse width and pulse rate, within an adjustment range specified by the clinician via the clinician programmer 22.

The neurostimulator 20, clinician programmer 22, and patient programmer 23 may communicate via wireless communication, as shown in FIG. 2B. The clinician programmer 22 and patient programmer 23 may, for example, communicate via wireless communication with neurostimulator 20 using RF telemetry techniques known in the art. The clinician programmer 22 and patient programmer 23 also may communicate with each other using any of a variety of local wireless communication techniques, such as RF communication according to the 802.11 or Bluetooth specification sets, or other standard or proprietary telemetry protocols. It is also understood that although FIG. 2B illustrates the patient programmer 22 and the clinician programmer 23 as two separate devices, they may be integrated into a single programmer in some embodiments.

The various aspects of the present disclosure will now be discussed in more detail below.

Figure 3A:
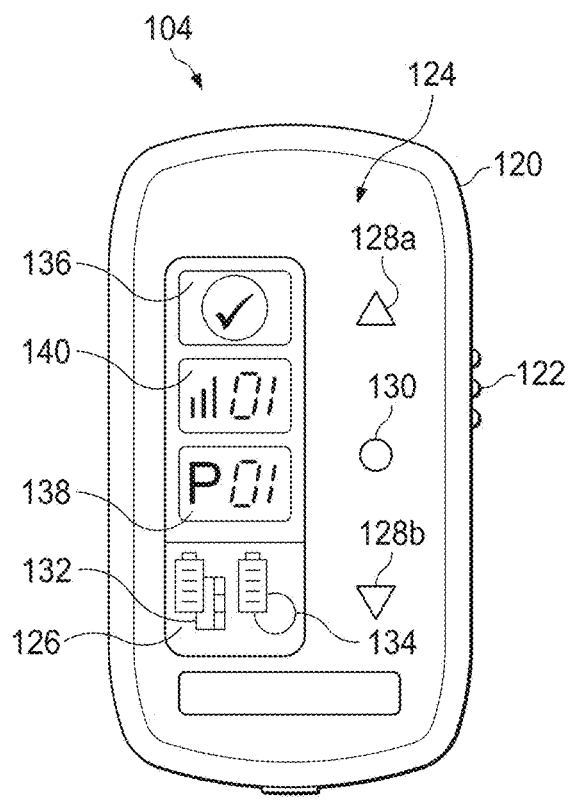
FIGS. 3A-3B illustrate an example pocket programmer controller in accordance with one embodiment of the present disclosure.
Figure 3B:
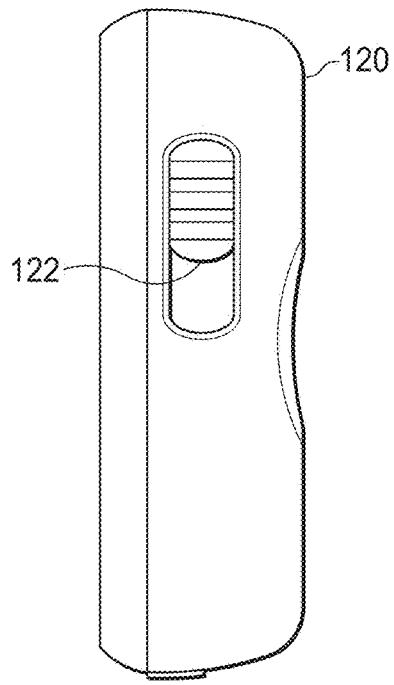
Figure 4:
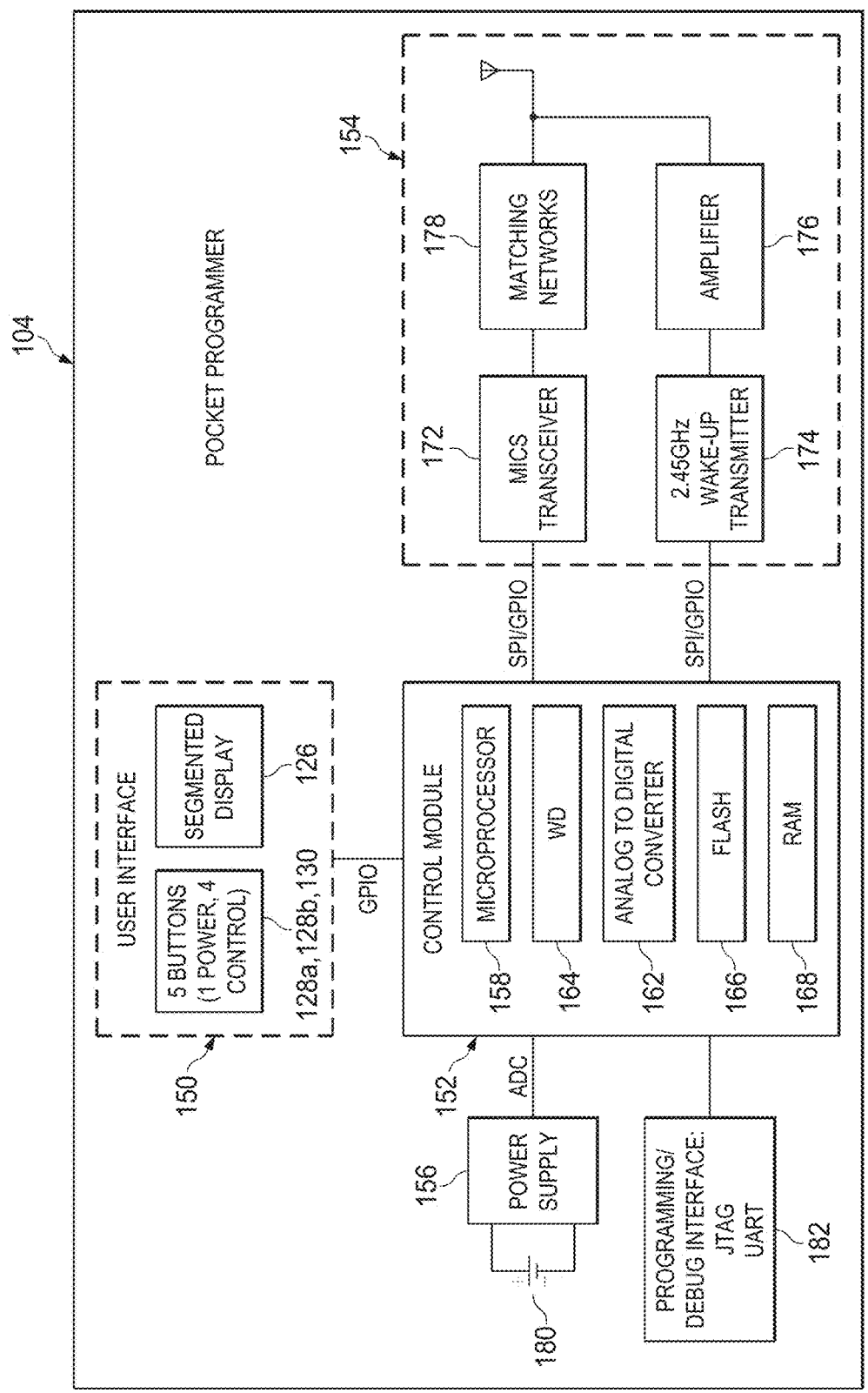
FIG. 4 is a block diagram of components of the example pocket controller of FIGS. 3A-3B in accordance with one embodiment of the present disclosure.
Figure 5A:
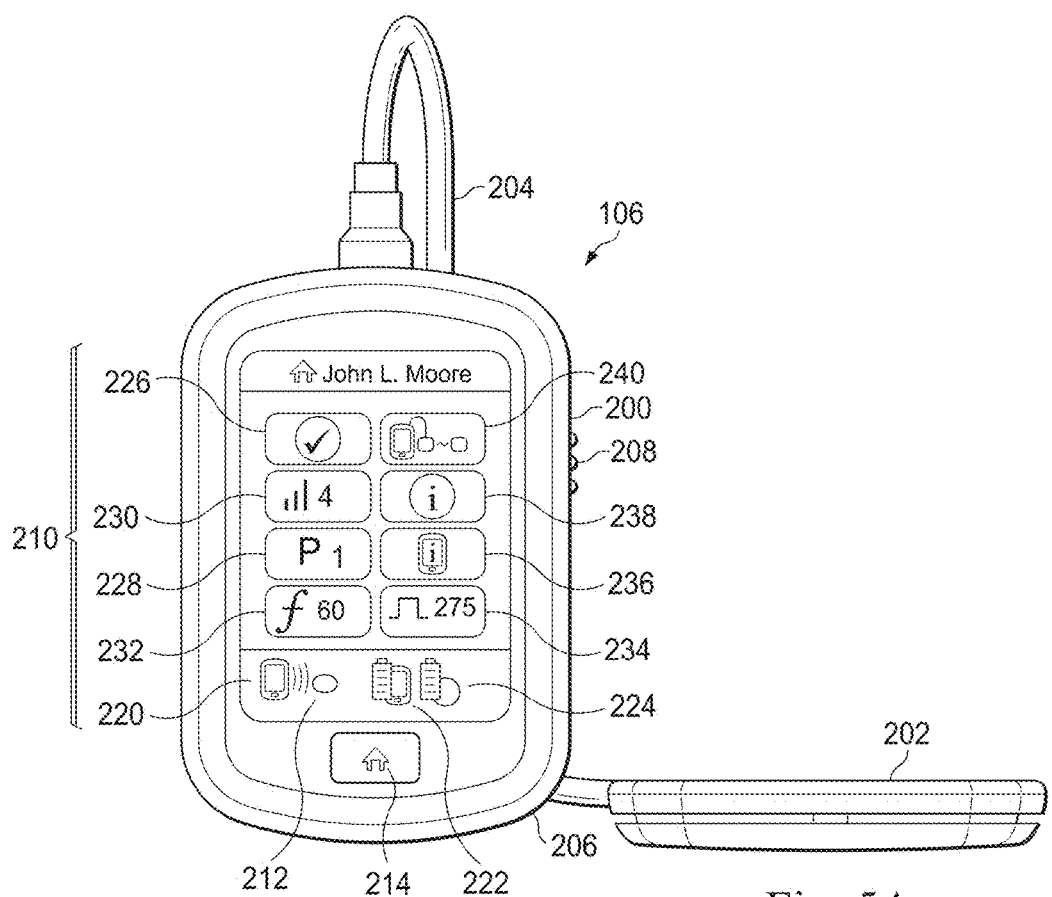
FIGS. 5A-5B illustrate an example patient programmer charger controller in accordance with one embodiment of the present disclosure.
Figure 5B:
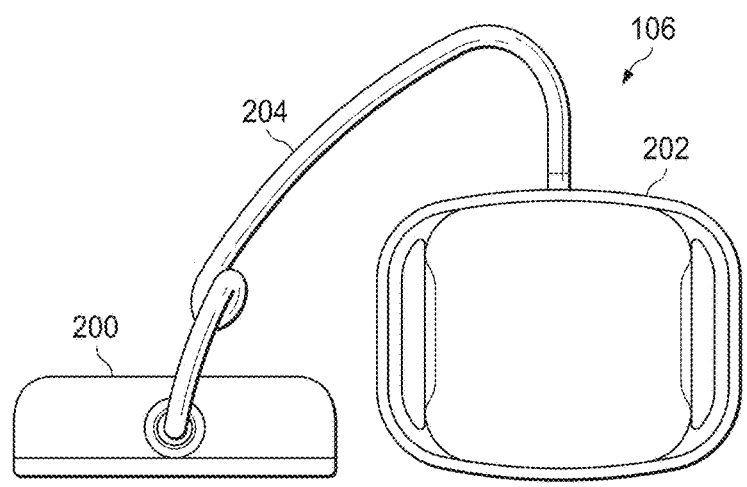
Figure 6:
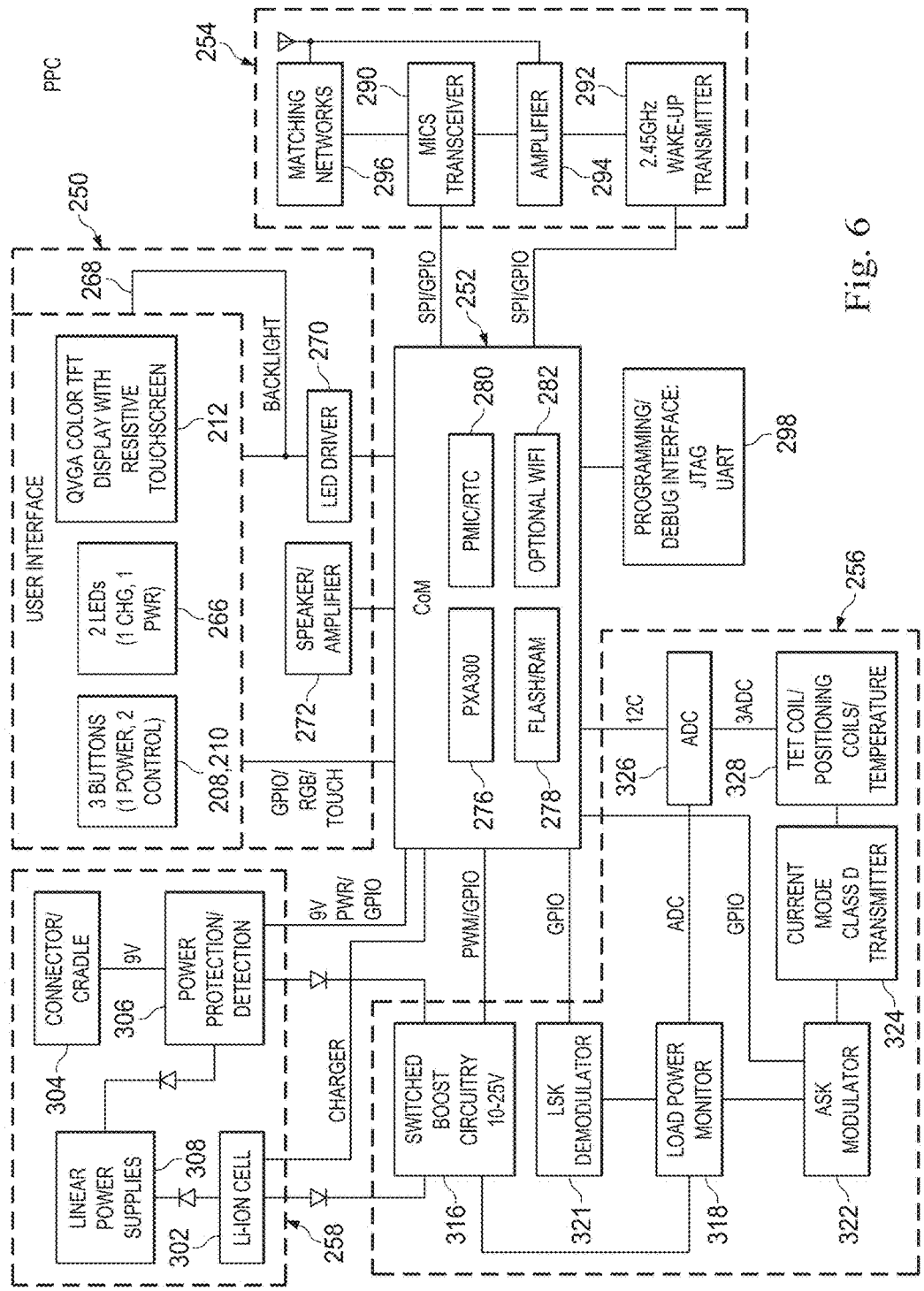
FIG. 6 is a block diagram of components of the example patient programmer charger of FIGS. 5A-5B in accordance with one embodiment of the present disclosure.

FIGS. 3A-3B, 4, 5A-5B, and 6 illustrate various example embodiments of the patient pocket programmer 22 (hereinafter referred to as patient programmer for simplicity) according to various aspects of the present disclosure. In more detail, FIGS. 3A-3B, 4 are directed to a patient programmer that is implemented as a pocket controller 104, and FIGS. 5A-5B and 6 are directed to a patient programmer that is implemented as a patient programmer charger (PPC) 106.

Referring now to FIGS. 3A and 3B, the pocket controller 104 comprises an outer housing 120 having an on-off switch 122, a user interface comprising a plurality of control buttons 124, and a display 126. In this embodiment, the housing 120 is sized for discreetness and may be sized to fit easily in a pocket and may be about the same size as a key fob. In one example, the housing 120 forming the pocket controller 104 has a thickness of less than about 1.5 inch, a width of less than about 1.5 inch, and a height of less than about 3 inches. In another example, the housing 120 forming the pocket controller 104 has a thickness of about 0.8 inch, a width of about 1.4 inch, and a height of about 2.56 inch. However, both larger and smaller sizes are contemplated.

In this example, the control buttons 124 include two adjustment buttons 128a, 128b, a select button 130, and an emergency off button (not shown, but disposed on a side of the housing 120 opposing the on-off switch 122). The two adjustment buttons 128a, 128b allow a user to scroll or highlight available options and increase or decrease values shown on the display 126. The select button 130 allows a user to enter the value or select the highlighted options to be adjusted by actuation of the adjustment buttons 128a, 128b. In this example, the buttons 128a, 128b are used to navigate to one of the three available functions: 1) electrical stimulation on/off, 2) control stimulation amplitude adjustment, and 3) electrical stimulation program selection. Once the desired function is highlighted, the select button is pushed to allow changes (i.e. change the stimulation amplitude, select a different stimulation program, or turn the electrical stimulation on or off). In some examples, the IPG control functions of the pocket controller 104 consist of these functions. The emergency off button is disposed for easy access for a patient to turn off stimulation from the IPG 102 if the IPG provides too much stimulation or stimulation becomes uncomfortable for the patient. Allowing the user to scroll through the plurality of options (also referred to herein as operational parameters) that can be adjusted via the pocket controller 104 provides the user the confidence to carry only the pocket controller 104 while away from home. Users may be reluctant to carry only a conventional controller that allows adjustment of only a single operational parameter out of fear that they may need to adjust a different operational parameter while away from a more full-featured controller.

In the embodiment shown, the display 126 is an LCD display arranged to convey information to the user regarding selectable options, present settings, operating parameters and other information about the IPG 102 or the pocket controller 104. In this example, the display 126 shows the pocket controller's battery status at 132, the IPG's battery status at 134, the IPG's on or off status at 136, the currently selected electrical stimulation program at 138, and the amplitude setting of the running electrical stimulation program at 140. Other types of displays are also contemplated.

FIG. 4 shows a block diagram of components making up the pocket controller 104. It includes a user interface 150, a control module 152, a communication module 154, and a power storing controller 156. The user interface 150 is comprised of the buttons 128a, 128b, 130 and the display 126 described above with reference to FIG. 3A.

As can be seen, the user interface 150 is in communication with the control module 152. The control module 152 comprises a processor 158, memory, an analog-digital converter 162, and a watch dog circuit 164. The processor 158 may include a microprocessor, a controller, a digital signal processor (DSP), an application specific integrated circuit (ASIC), a field programmable gate array (FPGA), discrete logic circuitry, or the like. The processor 158 is configured to execute code or instructions provided in the memory. Here, the memory is comprised of flash memory 166 and RAM memory 168. However, the memory may include any volatile or non-volatile media, such as a random access memory (RAM), read only memory (ROM), non-volatile RAM (NVRAM), electrically erasable programmable ROM (EEPROM), flash memory, and the like. In some embodiments, the memory stores sets of stimulation control parameters that are available to be selected for delivery through the communication module 154 to the IPG 102 for electrical stimulation therapy. The AD converter 162 performs known functions of converting signals and the WD 164 is arranged to time out when necessary, such as in an event where the software becomes stuck in a loop. In one embodiment, the control module 152 comprises integrated circuits disposed on a PC board.

The communication module 154 comprises a medical implant communication service (MICS) RF transceiver 172 used to communicate with the IPG 102 to communicate desired changes and to receive status updates from and relating to the IPG 102, such as battery status and any error information. As used herein, MICS refers to wireless communications in a frequency band ranging from about 402 MHz to about 405 MHz, which is dedicated for communications with implanted medical devices. In this example, the MICS RF transceiver 172 utilizes a loop antenna for the communications with the IPG 102. Other antennas, such as, for example, dipole, chip antennas, or other known in the art also may be used. The communication module 154 also includes a wake up transmitter 174, an amplifier 176, and matching networks 178. The wake up transmitter 174 operates on a high frequency and is configured to send a short signal burst to wake up the IPG 102 when it is in a power-saving mode. Once the IPG 102 is ready, a communications link can be established between the IPG 102 and pocket controller 104, and communications can then occur over the MICS transceiver 172 using a standard frequency for a medical device transmission. The matching networks 178 tunes the antenna for optimum transmission power for the frequency selected. The pocket controller 104 also includes a programming interface 182. This may be used during manufacturing to load an operating system and program the pocket controller 104.

The power storing controller 156 is configured to convert power to recharge one or more rechargeable batteries 180. The batteries 180 provide power to operate the pocket controller 104 allowing it to receive user inputs and transmit control signals to the IPG 102. Some embodiments use primary cell batteries instead of rechargeable batteries. As indicated above, this pocket controller 104 is part of a larger system that contains the PPC 106 with a rich feature set for controlling the IPG 102 and includes an integrated battery charger used to charge the IPG's battery. By providing both the pocket controller 104 and the PPC 106, the patient can have a small unobtrusive device to carry around as they go about their daily business and a larger more full featured device which they can use in the comfort and privacy of their homes.

The pocket controller 104 is not only comfortable to carry in a pocket, but can also be attached to a key ring, lanyard, or other such carrying device for ease of daily use. Its functions are a subset of functions found on the PPC 106, and permit a user to power stimulation from the IPG on and off (i.e., the IPG 102 remains on, but stimulation is toggled between the on state when the IPG 102 is emitting electrical pulses and the off state when the IPG 102 is not emitting electrical pulses but remains in the standby mode for additional communications from the pocket controller 104, the PPC 106, or both), select which electrical stimulation program to run, and globally adjust the amplitude of electrical pulses emitted in a series of electrical pulses emitted by the IPG 102. By limiting the functions of the pocket controller to those most commonly used on a daily basis, the device becomes much less intimidating to the patient, and allows it to be kept very small. By keeping the device small, such as about key fob size, it becomes unobtrusive and the patient is more comfortable with having and using an implanted device.

FIGS. 5A-5B show the PPC 106 in greater detail. FIG. 5A is a front view of the PPC and FIG. 5B is a top view of FIG. 5A. The PPC 106 performs all the same operating functions as the pocket controller 104, but includes additional operating functions making it a multi-function full-featured, advanced patient controller charger. In the embodiment shown, the PPC 106 provides a simple but rich feature set to the more advanced user, along with the charging functions.

The PPC 106 includes a controller-charger portion 200 and a coil portion 202 connected by a flexible cable 204 and sharing components as described below. The controller-charger portion 200 comprises an outer housing 206 having an on-off switch 208 on its side, a plurality of control buttons 210, and a display 212, and an emergency off button (not shown, but disposed on a side of the housing 206 opposing the on-off switch 208). In this embodiment, the control buttons 210 are icons on the display 212, and the display is a full color, touch screen, graphical user interface. In addition, the controller-charger portion 200 includes a home button 214 configured to return the displayed images to a home screen. The controller-charger portion 200 is larger than the pocket controller 104 and in one embodiment is sized with a height greater than about 3 inches, a width greater than about 2.5 inches, and a thickness greater than about 0.8 inch. In another embodiment, the controller-charger portion is sized with a width of about 3.1 inches, a height of about 4.5 inches, and thickness of about 0.96 inches, although both larger and smaller sizes are contemplated.

In this example, the control buttons 210 allow a user to select a desired feature for control or further display. Particularly, the control buttons 210 enable functions of the PPC 106 that are the same as those of the pocket controller 104 (stimulation on/off, program stimulation amplitude adjustment, and stimulation program selection) along with additional features including: charging IPG battery, individual pulse stimulation amplitude adjustment that adjusts an amplitude of an individual pulse relative to the amplitude of art adjacent pulse in a series of pulses emitted by the IPG 102, stimulation program frequency adjustment, individual pulse width adjustment, detailed IPG status, detailed. PPC status, PPC setup/configuration, a PPC battery status indicator, PPC to IPG communication status indicator, and other items and functions. The detailed IPG status may include, for example, IPG serial number and IPG software revision level. Detailed PPC status may include, for example, date and time setting, brightness control, audio volume and mute control, and PPC serial number and software revision level.

By having a pocket controller 104 that is limited to a plurality, such as only three controls (stimulation on/off, program amplitude adjust, and stimulation program selection), for example, a user can quickly and easily identify and select the features that are most commonly used. Features that are used less frequently, such as IPG recharge, are included on the full-featured PPC, but not the pocket controller 104. Features that are seldom accessed, or not accessed at all by some users, including individual pulse amplitude adjust, pulse width adjust, stimulation program frequency adjust, or serial number and software revision information, are also not included on the limited-feature pocket controller, but are included on the PPC. This allows the pocket controller to be significantly smaller, with a very simple and easy to user interface, as compared to systems that need to support all of these features.

Referring to the example shown in FIG. 5A, the touch screen display 212 is arranged to convey information to the user regarding selectable options, current settings, operating parameters and other information about the IPG 102 or the PPC 106. In this example, the display 212 shows a MICS communication indicator 220, the PPC's battery status at 222, the IPG's battery status at 224, the IPG's on or off status at 226, the currently selected electrical stimulation program at 228, and the amplitude setting of the active electrical stimulation program at 230. In addition, the display 212 shows the frequency 232, the pulse width setting 234, a selectable status icon for accessing detailed PPC information 236, a selectable status icon for accessing detailed IPG information 238, and a selectable icon for enabling IPG charging 240. Selecting any single icon may activate another menu within that selected subject area. The controller-charger portion 200 may include a rechargeable battery whose charge status is shown by the PPC's battery status at 222.

The coil portion 202 is configured to wirelessly charge the batteries in the IPG 102. In use, the coil portion 202 is applied against the patient's skin or clothing externally so that energy can be inductively transmitted and stored in the IPG battery. As noted above, the coil portion 202 is connected with the integrated controller-charger portion 200. Accordingly, the controller-charger portion 200 can simultaneously display the current status of the coil portion 204, the battery power level of the IPG 102, as well as the battery power level of the PPC. Accordingly, controlling and charging can occur in a more simplistic, time-effective manner, where the patient can perform all IPG maintenance in a single sitting. In addition, since the most commonly used features of the PPC 106 are already functional on the pocket controller, the PPC 106 may be left at home when the user does not desire to carry the larger, more bulky PPC.

FIG. 6 shows a block diagram of the components making up the PPC 106. It includes a user interface 250, a control module 252, a communication module 254, an IPG power charging module 256, and a power storing module 258. The user interface 250 is comprised of the buttons 210 and the display 212 described above. In this embodiment however, the user interface 250 also includes one or more LEDs 266 signifying whether the PPC 106 is charging or powered on and a backlight 268 that illuminates the color display. In some embodiments, these LEDs may have colors symbolizing the occurring function. An LED driver 270 and a speaker or amplifier 272 also form a part of the user interface 250.

As can be seen, the user interface 250 is in communication with the control module 252. The control module 252 comprises a processor 276, memory 278, and a power management integrated circuit (PMIC)/real time clock (RTC) 280. In the example shown, the control module 252 also includes a Wi-Fi RIP transceiver 282 that allows the PPC 106 to connect to a wireless network for data transfer. For example, it may permit doctor-patient interaction via the internet, remote access to PPC log files, remote diagnostics, and other information transfer functions. The PMIC 280 is configured to control the charging aspects of the PPC 106. The Wi-Fi transceiver 282 enables Wi-Fi data transfer for programming the PPC 106, and may permit wireless access to stored data and operating parameters. Some embodiments also include a Bluetooth RF transceiver for communication with, for example, a Bluetooth enabled printer, a keyboard, etc.

In one embodiment, the control module 252 also includes an AD converter and a watch dog circuit as described above with reference to the control module 252. Here, the memory 278 is comprised of flash memory and RAM memory, but may be other memory as described above. In some embodiments, the processor 276 is an embedded processor running a WinCE operating system (or any real time OS) with the graphics interface 250, and the memory 278 stores sets of stimulation control parameters that are available to be selected for delivery through the communication module 254 to the IPG 102 for electrical stimulation therapy. In one embodiment, the control module 252 comprises integrated circuits disposed on a PC board.

The communication module 254 comprises a MICS RF transceiver 290, a wake up transmitter 292, an amplifier 294, and matching networks 296. The communication module 254 may be similar to the communication module 154 discussed above, and will not be further described here. The PPC 206 also includes a programming interface 298 that may be used during manufacturing to load an operating system and program the PPC 206.

The power storing module 258 is configured to convert power to recharge one or more rechargeable batteries 302. In this embodiment, the batteries 302 are lithium-ion cells that provide power to operate the PPC 106 allowing it to receive user inputs, transmit control signals to, and charge the IPG 102. The power storing module 258 includes a connector 304 for connecting to a power source, a power protection detection circuit 306 for protecting the PPC from power surges, and linear power supplies 308 for assisting with the electric transfer to charge the batteries 302. As can be seen, the control module 252 aids with the charging and is configured to monitor and send the battery charge level to the user interface 250 for display. The connector 304 connects the PPC, directly or indirectly, to a power source (not shown) such as a conventional wall outlet for receiving electrical current. In some embodiments, the connector 304 comprises a cradle.

The power charging module 256 communicates with the control module 252 and is arranged to magnetically or inductively charge the IPG 102. In the embodiments shown, it is magnetically or inductively coupled to the IPG 102 to charge rechargeable batteries on the IPG 102. The charging module 256 includes components in both the controller-charger portion 200 and the coil portion 202 (FIGS. 5A-5B). It includes switch boost circuitry 316, a load power monitor 318, an LSK demodulator 321, a ASK modulator 322, a current mode transmitter 324, an ADC 326, and coils 328. As can be seen, the control module 252 aids with the charging and is configured to monitor and send the IPG battery charge level to the user interface 250 for display.

In this embodiment, the coils 328 are disposed in the coil portion 202 and are configured to create magnetic or inductive coupling with components in the IPG 102. Since the coil portion 202 is integrated with the controller-charger portion 200, both operate from a single battery 302. Accordingly, as can be seen by the circuitry, the battery 302 powers the control module 252 and all its associated components. In addition, the battery 302 powers the power charging module 256 for recharging the IPG 102.

Because the coil portion 202 is integrated with the controller-charger portion 200, the control module 252 provides a single control interface and a single user interface for performing both functions of controlling the IPG 102 and of charging the IPG 102. In addition, because the controller-charger portion 200 and the coil portion 202 are integrated, the controller-charger portion 200 simultaneously controls both the current status of the charger, the battery power level of the IPG 102, as well as the battery power level of the PPC. Accordingly, controlling and charging can occur in a more simplistic, time-effective manner, where the patient can perform all IPG maintenance in a single sitting. In addition, since the most commonly used features of the PPC 106 are already functional on the pocket controller, the PPC 106 may be left at home when the user does not desire to carry the larger, more bulky PPC.

Figure 7:
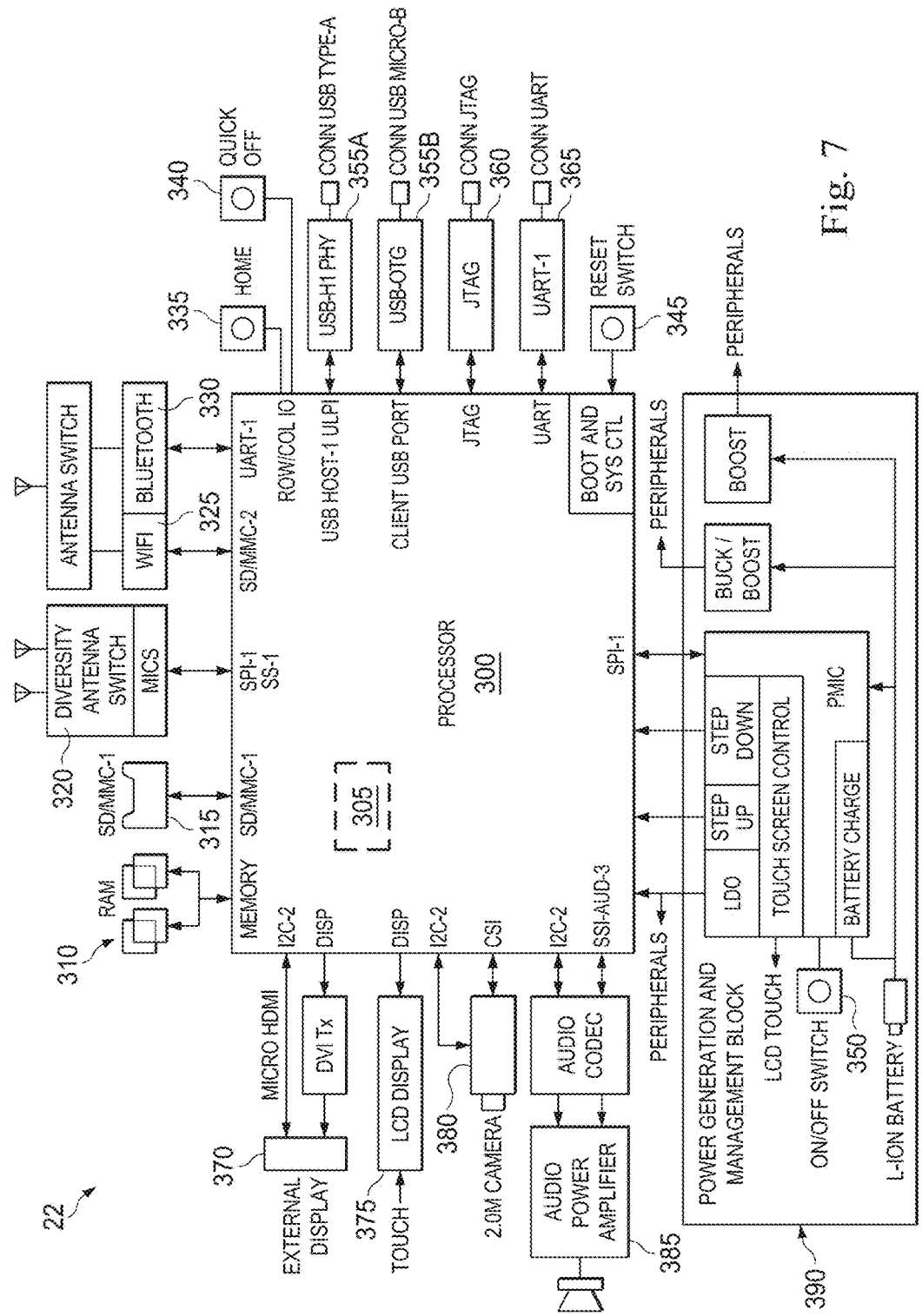
FIG. 7 is a block diagram of a clinician programmer according to one embodiment of the present disclosure.

FIG. 7 shows a block diagram of one example embodiment of a clinician programmer (CP), for example the CP 22 shown in FIG. 2B. The CP 22 includes a printed circuit board ("PCB") that is populated with a plurality of electrical and electronic components that provide power, operational control, and protection to the CP 22. With reference to FIG. 7, the CP includes a processor 300. The processor 300 is a controller for controlling the CP 22 and, indirectly, the IPG 20 as discussed further below. In one construction, the processor 300 is an applications processor model i.MX515 available from Freescale Semiconductor. More specifically, the i.MX515 applications processor has internal instruction and data cashes, multimedia capabilities, external memory interfacing, and interfacing flexibility. Further information regarding the i.MX515 applications processor can be found in, for example, the "IMX510EC, Rev. 4" data sheet; dated August 2010; published by Freescale Semiconductor at www.freescale.com, the content of the data sheet being incorporated herein by reference. Of course, other processing units, such as other microprocessors, microcontrollers, digital signal processors, etc., can be used in place of the processor 300.

The CP 22 includes memory, which can be internal to the processor 300 (e.g., memory 305), external to the processor 300 (e.g., memory 310), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 300 executes software that is capable of being stored in the RAM (e.g., during execution), the ROM (e.g., on a generally permanent basis), or another non-transitory computer readable medium such as another memory or a disc. The CP 22 also includes input/output ("I/O") systems that include routines for transferring information between components within the processor 300 and other components of the CP 22 or external to the CP 22.

Software included in the implementation of the CP 22 is stored in the memory 305 of the processor 300, memory 310 (e.g., RAM or ROM), or external to the CP 22. The software includes, for example, firmware, one or more applications, program data, one or more program modules, and other executable instructions. The processor 300 is configured to retrieve from memory and execute, among other things, instructions related to the control processes and methods described below for the CP 22. For example, the processor 300 is configured to execute instructions retrieved from the memory 140 for establishing a protocol to control the IPG 20.

One memory shown in 7 is memory 310, which can be a double data rate (DDR2) synchronous dynamic random access memory (SDRAM) for storing data relating to and captured during the operation of the CP 22. In addition, a secure digital (SD) multimedia card (MMC) can be coupled to the CP for transferring data from the CP to the memory card via slot 315. Of course, other types of data storage devices can be used in place of the data storage devices shown in FIG. 7.

The CP 22 includes multiple bi-directional radio communication capabilities. Specific wireless portions included with the CP 22 are a Medical Implant Communication Service (MICS) bi-direction radio communication portion 320, a Wi-Fi bi-direction radio communication portion 325, and a Bluetooth hi-direction radio communication portion 330. The MICS portion 320 includes a MICS communication interface, an antenna switch, and a related antenna, all of which allows wireless communication using the MICS specification. The Wi-Fi portion 325 and Bluetooth portion 330 include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP 22.

The CP 22 includes three hard buttons: a "home" button 335 for returning the CP to a home screen for the device, a "quick off" button 340 for quickly deactivating stimulation IPG, and a "reset" button 345 for rebooting the CP 22. The CP 22 also includes an "ON/OFF" switch 350, which is part of the power generation and management block (discussed below).

The CP 22 includes multiple communication portions for wired communication. Exemplary circuitry and ports for receiving a wired connector include a portion and related port for supporting universal serial bus (USB) connectivity 355, including a Type-A port and a Micro-B port; a portion and related port for supporting Joint Test Action Group (JTAG) connectivity 360, and a portion and related port for supporting universal asynchronous receiver/transmitter (DART) connectivity 365. Of course, other wired communication standards and connectivity can be used with or in place of the types shown in FIG. 7.

Another device connectable to the CP 22, and therefore supported by the CP 22, is an external display. The connection to the external display can be made via a micro High-Definition Multimedia Interface (HDMI) 370, which provides a compact audio/video interface for transmitting uncompressed digital data to the external display. The use of the HDMI connection 370 allows the CP 22 to transmit video (and audio) communication to an external display. This may be beneficial in situations where others (e.g., the surgeon) may want to view the information being viewed by the healthcare professional. The surgeon typically has no visual access to the CP 22 in the operating room unless an external screen is provided. The HDMI connection 370 allows the surgeon to view information from the CP 22, thereby allowing greater communication between the clinician and the surgeon. For a specific example, the HDMI connection 370 can broadcast a high definition television signal that allows the surgeon to view the same information that is shown on the LCD (discussed below) of the CP 22.

The CP 22 includes a touch screen I/O device 375 for providing a user interface with the clinician. The touch screen display 375 can be a liquid crystal display (LCD) having a resistive, capacitive, or similar touch-screen technology. It is envisioned that multitouch capabilities can be used with the touch screen display 375 depending on the type of technology used.

The CP 22 includes a camera 380 allowing the device to take pictures or video. The resulting image files can be used to document a procedure or an aspect of the procedure. For example, the camera 380 can be used to take pictures of barcodes associated with the IPG 20 or the leads 120, or documenting an aspect of the procedure, such as the positioning of the leads. Similarly, it is envisioned that the CP 22 can communicate with a fluoroscope or similar device to provide further documentation of the procedure. Other devices can be coupled to the CP 22 to provide further information, such as scanners or RFID detection. Similarly, the CP 22 includes an audio portion 385 having an audio codec circuit, audio power amplifier, and related speaker for providing audio communication to the user, such as the clinician or the surgeon.

The CP 22 further includes a power generation and management block 390. The power generation and management block 390 has a power source (e.g., a lithium-ion battery) and a power supply for providing multiple power voltages to the processor, LCD touch screen, and peripherals.

Figure 8:
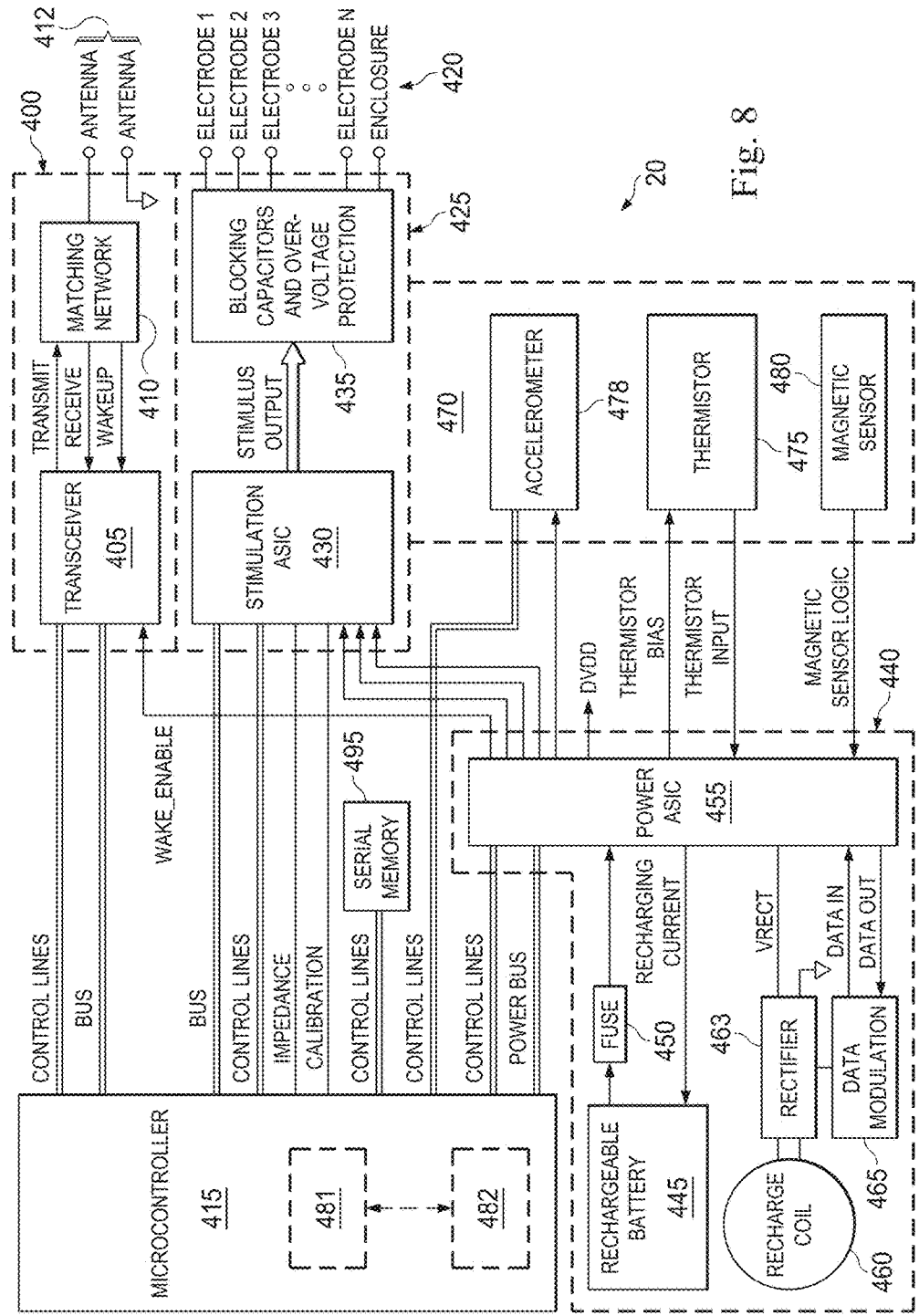
FIG. 8 is a block diagram of an implantable pulse generator according to one embodiment of the present disclosure.

FIG. 8 shows a block diagram of an example embodiment of an IPG, for example an embodiment of the IPG 20 shown in FIG. 2B. The IPG 20 includes a printed circuit board ("PCB") that is populated with a plurality of electrical and electronic components that provide power, operational control, and protection to the IPG 20. With reference to FIG. 8, the IPG 20 includes a communication portion 400 having a transceiver 405, a matching network 410, and antenna 412. The communication portion 400 receives power from a power ASIC (discussed below), and communicates information to/from the microcontroller 415 and a device (e.g., the CP 22) external to the IPG 20. For example, the IPG 20 can provide bi-direction radio communication capabilities, including Medical Implant Communication Service (MICS) bi-direction radio communication following the MICS specification.

The IPG 20, as previously discussed, provides stimuli to electrodes 150 of an implanted medical electrical lead 110. As shown in FIG. 8, N electrodes 150 are connected to the IPG 20. In addition, the enclosure or housing 420 of the IPG 20 can act as an electrode. The stimuli are provided by a stimulation portion 425 in response to commands from the microcontroller 415. The stimulation portion 425 includes a stimulation application specific integrated circuit (ASIC) 430 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, Flash, etc. The stimulation ASIC 430 can include a processor, memory, and firmware for storing preset pulses and protocols that can be selected via the microcontroller 415. The providing of the pulses to the electrodes 150 is controlled through the use of a waveform generator and amplitude multiplier of the stimulation ASIC 430, and the blocking capacitors and overvoltage protection circuitry of the stimulation portion 425, as is known in the art. The stimulation portion 425 of the IPG 20 receives power from the power ASIC (discussed below). The stimulation ASIC 430 also provides signals to the microcontroller 415. More specifically, the stimulation ASIC 430 can provide impedance values for the channels associated with the electrodes 150, and also communicate calibration information with the microcontroller 415 during calibration of the IPG 20.

The IPG 20 also includes a power supply portion 440. The power supply portion includes a rechargeable battery 445, fuse 450, power ASIC 455, recharge coil 460, rectifier 463 and data modulation circuit 465. The rechargeable battery 445 provides a power source for the power supply portion 440. The recharge coil 460 receives a wireless signal from the PPC 135. The wireless signal includes an energy that is converted and conditioned to a power signal by the rectifier 463. The power signal is provided to the rechargeable battery 445 via the power ASIC 455. The power ASIC 455 manages the power for the IPG 20. The power ASIC 455 provides one or more voltages to the other electrical and electronic circuits of the IPG 155. The data modulation circuit 465 controls the charging process.

The IPG also includes a sensor section 470 that includes a thermistor 475, an accelerometer 478, and a magnetic sensor 480. The thermistor 475 detects temperature of the IPG. The accelerometer 478 detects motion or movement of the IPG, and the magnetic sensor 480 provides a "hard" switch upon sensing a magnet for a defined period. The signal from the magnetic sensor 480 can provide an override for the IPG 20 if a fault is occurring with the IPG 20 and is not responding to other controllers. The magnetic sensor 480 can also be used to turn on and off stimulation.

The IPG 20 is shown in FIG. 8 as having a microcontroller 415. Generally speaking, the microcontroller 415 is a controller for controlling the IPG 20. The microcontroller 415 includes a suitable programmable portion 481 (e.g., a microprocessor or a digital signal processor), a memory 482, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG 20 includes memory, which can be internal to the control device (such as memory 482), external to the control device (such as serial memory 495), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 481 executes software that is capable of being stored in the RAM (e.g., during execution), the ROM (e.g., on a generally permanent basis), or another non-transitory computer readable medium such as another memory or a disc.

Software included in the implementation of the IPG 20 is stored in the memory 482. The software includes, for example, firmware, one or more applications, program data, one or more program modules, and other executable instructions. The programmable portion 481 is configured to retrieve from memory and execute, among other things, instructions related to the control processes and methods described below for the IPG 20. For example, the programmable portion 481 is configured to execute instructions retrieved from the memory 482 for sweeping the electrodes in response to a signal from the CP 22.

The PCB also includes a plurality of additional passive and active components such as resistors, capacitors, inductors, integrated circuits, and amplifiers. These components are arranged and connected to provide a plurality of electrical functions to the PCB including, among other things, filtering, signal conditioning, or voltage regulation, as is commonly known.

Figure 10A:
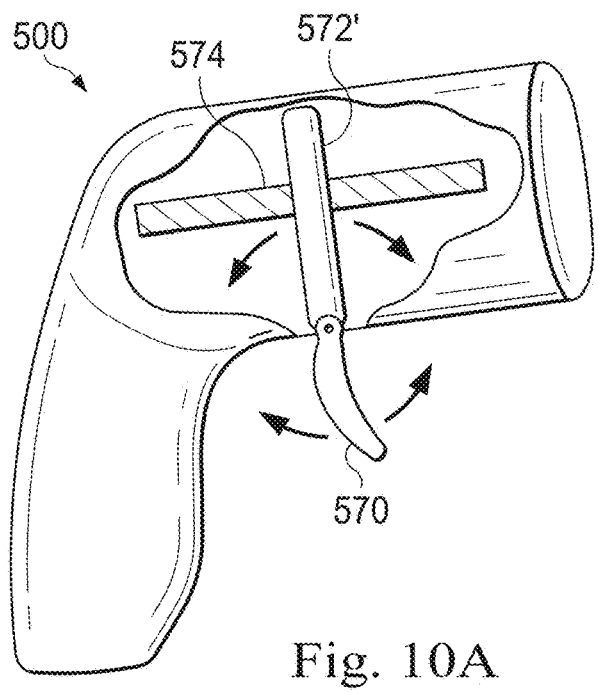
FIGS. 10A and 10B are exterior views of the patient feedback device according to embodiments of the present disclosure.
Figure 10B:
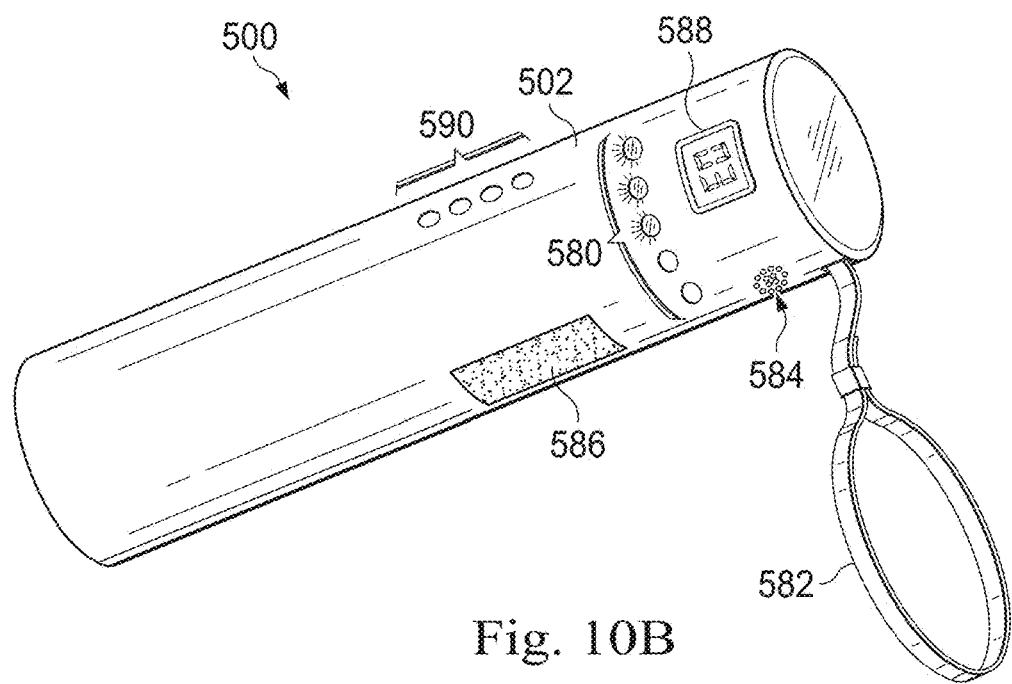

FIG. 9 is a block diagram of an exemplary handheld patient feedback device or patient feedback tool (hereinafter interchangeably referred to as PFD or PFT) 500 for use in a neurostimulation system, and FIGS. 10A and 10B are diagrammatic illustrations of the PFT 500 according to various example embodiments. With reference to FIGS. 9 and 10A-10B, the PFT 500 includes a housing 502 which may have one or more of a sensor, a controller, and/or a communication port connected thereto. The construction of the PFT 500 shown in FIG. 9 includes two inputs 504 and 505 in communication with the housing 502 of the device 500 and one input 510 internal to the housing 502. One of the external inputs 504 is a binary ON/OFF switch, for example activated by the patient's thumb, to allow the patient to immediately deactivate stimulation. Input 504 may be coupled to the controller 525 via electrostatic discharge (ESD) protection and/or debouncing circuits. The second input 505 includes a force sensor sensing the pressure or force exerted by the patient's hand. Input/sensor 505 may be coupled to the controller 525 via ESD protection, signal conditioning, and/or signal amplification circuits. The sensed parameter can be either isotonic (constant force, measuring the distance traversed) or isometric (measured force, proportional to pressure applied by patient). The resulting signal from the sensor 505 is analog and, therefore, after the signal is conditioned and/or amplified, it can be passed to microcontroller 525 via an analog-to-digital converter.

The internal input 510 for the PFT 500 may be a motion sensor. The sensor 510, upon detecting motion, initiates activation of the PFT 500. The device 500 stays active until movement is not detected by the sensor 510 for a time period, which in various constructions may be between one second and five minutes. Power is provided by an internal battery 520 that can be replaceable and/or rechargeable, which in various constructions has an approximately three hour life under continuous use. As discussed below, a motion sensor such as sensor 510 can also be used to obtain feedback from the patient regarding paresthesia.

The processing of the inputs from the sensors 504 and 505 takes place in a controller, such as a microcontroller 525. An exemplary microcontroller capable of being used with the invention is microcontroller 525, which includes a suitable programmable portion 530 (e.g., a microprocessor or a digital signal processor), a memory 535, and a bus 540 or other communication lines. Output data of the microcontroller 525 is sent via a Bluetooth bi-direction radio communication port 545 to the CP (clinician programmer). The Bluetooth portion 545 includes a Bluetooth communication interface, an antenna switch, and a related antenna, all of which allows wireless communication following the Bluetooth Special Interest Group standard. Other forms of wired and wireless communication between the PFT 500 and other components of the system including the CP are also possible. Other outputs may include indicators (such as light-emitting diodes) for communicating stimulation activity 550, sensor activation 555, device power 560, and battery status 565.

The housing 502 of the PFT 500 may be cylindrical in shape, and in one particular construction the cylinder is approximately 35 mm in diameter and 80 mm in length. In other constructions the cylinder is larger or smaller in diameter and/or length, for example in order to accommodate hands of varying sizes. In various constructions the diameter can range from 20 to 50 mm and the length from 30 to 120 mm, although other sizes above and below these ranges are also possible.

Furthermore, the shape of the PFT 500 can be other than a circular cross-section, for example oval, square, hexagonal, or other shape. Still further, the cross-section of the PFT 500 can vary along its length, for example being cylindrical in some portions and oval, square, hexagonal or other shape(s) in other portions. In yet other constructions, the PFT 500 has a spherical, torpid, or other shape.

The housing 502 may be made from a resilient material such as rubber or plastic with one or more sensors 505 coupled to or supported by the housing 502. The manner in which the sensor 505 is coupled to the housing 502 depends on the type of sensor that is employed, as discussed below. Thus, when the patient applies a force to the housing 502, the sensor 505 generates a signal that generally is proportional to the degree of force applied. Although the discussion herein mentions the patient using his or her hand to generate force to squeeze the housing 502 of the PFT 500, in various constructions the patient may instead use other body parts, such as the mouth or foot, to generate force. More generally, the patient can generate feedback by a physical action, usually a force applied by the hand or other body part, but the physical action can include other movements, such as movement of the patient's eyes, head, or hands, to generate a feedback signal.

After the signal is generated, it is transmitted from the sensor 505 to the controller 525. The controller 525 processes the signal and, based on one or more such signals from the sensor 505, the controller 525 generates another signal that is to be transmitted to the CP. The controller 525 sends the signal to be transmitted to the communication port 545 of the PFT 500 from which it is then transmitted to the CP or other external device. As discussed further below, the signal can be transmitted from the communication port 545 to the CP using various wired or wireless methods of communication.

In various constructions, an isotonic force sensor may include a sensor that measures the distance traveled by the sensor with relatively constant force applied by the patient. Isotonic force sensors may include a trigger 570 (See FIG. 10A) or other lever mechanism coupled to a wiper 572 that moves along a rheostat 571 or across a series of detectors. Exemplary detectors include electrical contacts or optical detectors, such as photodiodes. In other constructions, an isometric force sensor may include a strain gauge, a piezoelectric device, or a pressure sensor, each of which measures force that is proportional to the pressure applied to the PFT 500 by the patient, generally with only a small amount of travel or shape change to the sensor.

Both the isotonic and isometric sensors generate an electrical signal that is proportional to the force that is applied to the sensor. An isometric force sensor may be incorporated into a relatively stiff object such that only slight deformation of the object is needed to register a change in force. In still other constructions, the force sensor may include a combination of elements, such as a trigger or other lever that experiences increasing resistance or pressure as the travel distance increases. For example, increasing resistance or pressure can be created by attaching a relatively stiff spring to the lever or wiper mechanism to increase resistance as the lever or wiper is moved.

In some constructions (e.g. as shown in FIG. 10B), the PFT 500 includes a feedback mechanism 580 that indicates to the patient the amount of force that is detected by the force sensor 505. The feedback mechanism 580 may include one or more of a visual, audible, or tactile feedback mechanism that is used to indicate to the patient the degree to which the sensor 505 has been activated, e.g., how much force has been applied or how much the lever or wiper mechanism has traveled. The feedback mechanism gives the patient a sense of whether their activation of the sensor 505 is being detected at what the patient feels is the correct level and to give the patient a means to make their activation of the sensor 505 more consistent.

Visual feedback mechanisms 580 can include a series of lights (e.g. LEDs) or a digital readout (e.g. a numerical display); audible feedback can include sounds that vary in amplitude (volume) and/or tone; and tactile feedback mechanisms can include vibration of the PFT 500 and/or altering the shape of the surface of the PFT 500 (e.g. raising of one or more structures such as dots to form Braille-type patterns) in a location that is capable of contacting the patient's skin. Using a combination of feedback modalities will benefit patients who have sensory impairments, including, e.g., impaired hearing and/or sight.

The feedback can include a semi-quantitative indication of the patient's response, e.g. including a variety of (e.g. 1-5 or 1-10) intensity levels to indicate a relative degree of force applied by the patient. The patient will then be able to see, hear, and/or feel the level of force that is sensed by the sensor 505 of the PFT 500, to help the patient confirm that their response to the stimulus was received, as well as the degree of response that was registered. The correlation between the level of force applied and the output of the feedback mechanism 580 can be calibrated separately for each patient during an initial calibration session.

To facilitate gripping of the PFT 500, the housing 502, in certain constructions, may be covered with one or more surfaces, textures, or materials to improve grip, such as grooves, stipples, indentations, rubber, or plastic, and may include a wrist strap 582 to keep the PFT 500 from falling if it is dropped by the patient.

The PFT 500, in some constructions, may also include a connection feedback mechanism, particularly where the PFT 500 is in wireless communication with the CP. The connection feedback mechanism can include one or more of a visual, audible, or tactile mechanism to inform the patient and/or medical personnel of whether the PFT 500 is maintaining a connection with the CP, the strength of the connection, and/or if the connection has been lost. For example, the PFT 500 may emit a signal (e.g., light, sound, and/or tactile) at regular (e.g., one minute) intervals to confirm that communication is still maintained.

Conversely, the PFT 500 may emit such a signal only if communication is lost. In some constructions, the PFT 500 may tolerate brief intervals in which the signal is lost (e.g., a predetermined time, generally between 0.1-100 sec) before the patient is warned of a possible lost connection. In various constructions, the controller 525 of the PFT 500 includes memory that permits buffering of a limited amount of data, which can be used to accumulate data prior to sending to the CP and which can hold data during brief intervals in which the connection is lost. In various constructions, if communication between the PFT 500 and the CP is lost for more than a predetermined interval of time, then the CP stops stimulation of electrodes until a connection with the PFT 500 is reestablished.

Thus, according to various constructions, the PFT 500 may include one or more of: a sound generating mechanism 584 (e.g., a speaker); a tactile mechanism 586 such as a vibration device and/or a mechanism for creating a raised pattern; a digital numerical readout 588 (e.g., LED or LCD display); and one or more indicator lights 590 (e.g., a series of LEDs); which may be employed to provide feedback to the patient regarding the force being applied and/or communication status.

Various types of sensing mechanisms can be used for the sensor 505, which would depend in part on the type of housing 502 that is used with the PFT 500. For example, if the housing 502 is a sealed, flexible compartment (e.g., a ball or other object filled with gel, air, or liquid) a piezoelectric-based pressure sensing mechanism can be used as the sensor 505 in order to measure changes in pressure when the patient squeezes or relaxes his/her grip on the PFT 500. Alternatively, a rheostat 574 or other linear sensing mechanism can be used with a pistol grip style PFT 500 design (FIG. 10A), where a trigger 570 is coupled to a wiper 572 that moves across the rheostat 574 or other linear sensor.

Figure 11B:
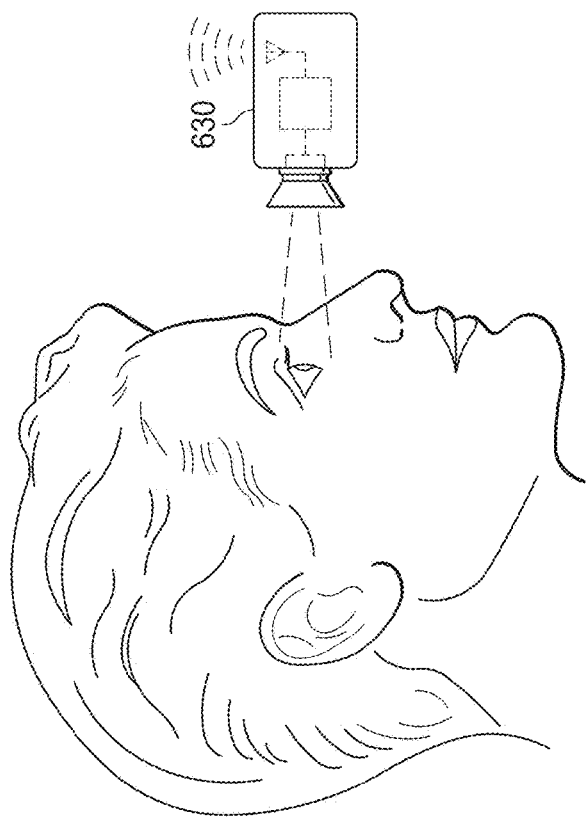
FIG. 11B is a side view of a patient-feedback device with optical sensing according to an embodiment of the present disclosure.
Figure 11A:
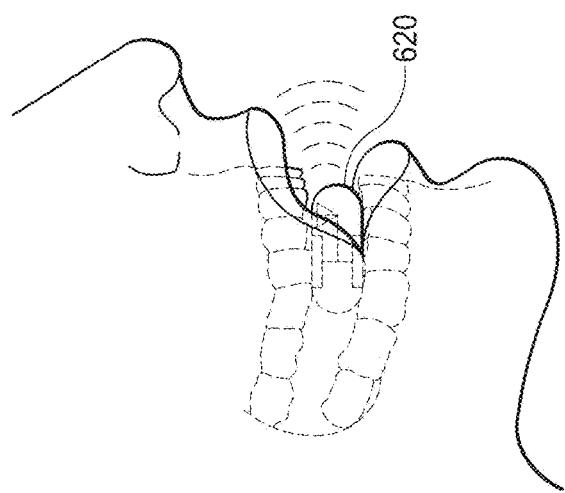
FIG. 11A is a side view of a patient-feedback device inserted in the mouth of a patient according to an embodiment of the present disclosure.
Figure 11C:
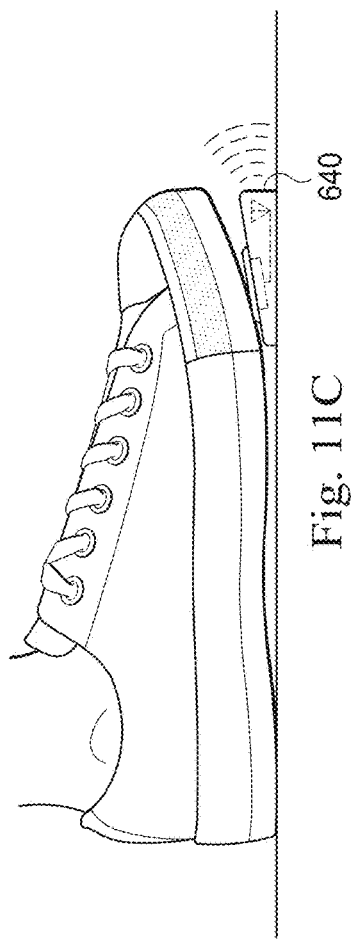
FIG. 11C is a side view of a patient-feedback device activated by a foot of a patient according to an embodiment of the present disclosure.

FIGS. 11A-11C illustrate other embodiments of the PFT for receiving patient feedback. More specifically, FIG. 11A shows a mouth-piece 620 that is inserted into the mouth of the patient. The user provides feedback by biting the mouth-piece. FIG. 11B shows an optical sensor 630 (such as a camera and related image processing software) that detects visual cues from a patient. An example visual cue may be the blinking of the patient's eyes. FIG. 11C shows a foot pedal 640 that receives input through the patient's manipulation of a switch and/or sensor with his foot. In some constructions, the PFT 500 includes one or more accelerometers (such as the motion sensor 510), and the patient provides feedback by moving the PFT 500 in various distinct patterns that are recognized by the controller 525 of the PFT 500 or by the CP.

It is also envisioned that the patient may provide feedback directly to the CP. In various constructions, the patient is trained to use the particular feedback device (e.g. the PFT 500 or the CP as applicable) in order to properly inform the CP of the patient's reaction to stimuli as they are applied to the IPG in the patient. In particular constructions, the CP is programmed to learn the patient's response times and/or the magnitude of the patient's responses in order to obtain a profile of the patient's reaction to various stimuli, as discussed above.

Figure 12:
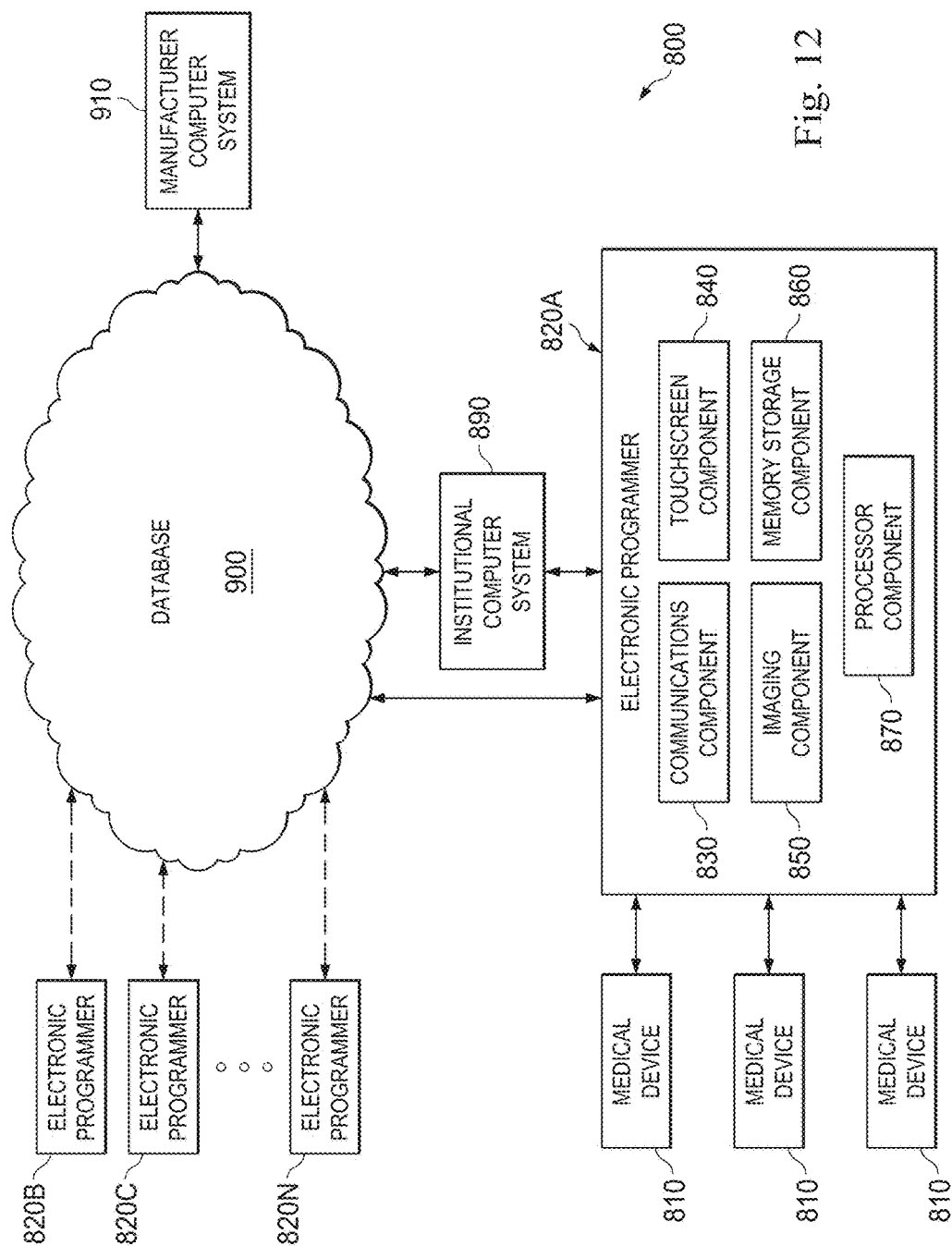
FIG. 12 is a simplified block diagram of a medical system/infrastructure according to various aspects of the present disclosure.

Referring now to FIG. 12, a simplified block diagram of a medical infrastructure 800 (which may also be considered a medical system) is illustrated according to various aspects of the present disclosure. The medical infrastructure 800 includes a plurality of medical devices 810. These medical devices 810 may each be a programmable medical device (or parts thereof) that can deliver a medical therapy to a patient. In some embodiments, the medical devices 810 may include a device of the neurostimulator system discussed above. For example, the medical devices 810 may be a pulse generator (e.g., the IPG discussed above), an implantable lead, a charger, or portions thereof. It is understood that each of the medical devices 810 may be a different type of medical device. In other words, the medical devices 810 need not be the same type of medical device.

The medical infrastructure 800 also includes a plurality of electronic programmers 820. For sake of illustration, one of these electronic programmers 820A is illustrated in more detail and discussed in detail below. Nevertheless, it is understood that each of the electronic programmers 820 may be implemented similar to the electronic programmer 820A.

In some embodiments, the electronic programmer 820A may be a clinician programmer, for example the clinician programmer discussed above with reference to FIGS. 2B and 7. In other embodiments, the electronic programmer 820A may be a patient programmer discussed above with reference to FIGS. 2B-6. In further embodiments, it is understood that the electronic programmer may be a tablet computer. In any case, the electronic programmer 820A is configured to program the stimulation parameters of the medical devices 810 so that a desired medical therapy can be delivered to a patient.

The electronic programmer 820A contains a communications component 830 that is configured to conduct electronic communications with external devices. For example, the communications device 830 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (Wi-Fi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 820A contains a touchscreen component 840. The touchscreen component 840 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 820A may optionally include additional user input/output components that work in conjunction with the touchscreen component 840 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HIM ports), joy-sticks, etc.

The electronic programmer 820A contains an imaging component 850. The imaging component 850 is configured to capture an image of a target device via a scan. For example, the imaging component 850 may be a camera in some embodiments. The camera may be integrated into the electronic programmer 820A. The camera can be used to take a picture of a medical device, or scan a visual code of the medical device, for example its barcode or Quick Response (QR) code.

The electronic programmer contains a memory storage component 860. The memory storage component 860 may include system memory, (e.g., RAM), static storage (e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 860 (or a portion thereof) may be configured as a local database capable of storing electronic records of medical devices and/or their associated patients.

The electronic programmer contains a processor component 870. The processor component 870 may include a central processing unit (CPU), a graphics processing unit (GPU) a micro-controller, a digital signal processor (DSP), or another suitable electronic processor capable of handling and executing instructions. In various embodiments, the processor component 870 may be implemented using various digital circuit blocks (including logic gates such as AND, OR, NAND, NOR, XOR gates, etc.) along with certain software code. In some embodiments, the processor component 870 may execute one or more sequences computer instructions contained in the memory storage component 860 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 820A is not necessarily limited to the components 830-870 discussed above, but it may further include additional components that are used to carry out the programming tasks. These additional components are not discussed herein for reasons of simplicity. It is also understood that the medical infrastructure 800 may include a plurality of electronic programmers similar to the electronic programmer 820A discussed herein, but they are not illustrated in FIG. 12 for reasons of simplicity.

The medical infrastructure 800 also includes an institutional computer system 890. The institutional computer system 890 is coupled to the electronic programmer 820A. In some embodiments, the institutional computer system 890 is a computer system of a healthcare institution, for example a hospital. The institutional computer system 890 may include one or more computer servers and/or client terminals that may each include the necessary computer hardware and software for conducting electronic communications and performing programmed tasks. In various embodiments, the institutional computer system 890 may include communications devices (e.g., transceivers), user input/output devices, memory storage devices, and computer processor devices that may share similar properties with the various components 830-870 of the electronic programmer 820A discussed above. For example, the institutional computer system 890 may include computer servers that are capable of electronically communicating with the electronic programmer 820A through the MICS protocol or another suitable networking protocol.

The medical infrastructure 800 includes a database 900. In various embodiments, the database 900 is a remote database that is, located remotely to the institutional computer system 890 and/or the electronic programmer 820A. The database 900 is electronically or communicatively (for example through the Internet) coupled to the institutional computer system 890 and/or the electronic programmer. In some embodiments, the database 900, the institutional computer system 890, and the electronic programmer 820A are parts of a cloud-based architecture. In that regard, the database 900 may include cloud-based resources such as mass storage computer servers with adequate memory resources to handle requests from a variety of clients. The institutional computer system 890 and the electronic programmer 820A (or their respective users) may both be considered clients of the database 900. In certain embodiments, the functionality between the cloud-based resources and its clients may be divided up in any appropriate manner.

For example, the electronic programmer 820A may perform basic input/output interactions with a user, but a majority of the processing and caching may be performed by the cloud-based resources in the database 900. However, other divisions of responsibility are also possible in various embodiments.

According to the various aspects of the present disclosure, various types of data may be uploaded from the electronic programmer 820A to the database 900. The data saved in the database 900 may thereafter be downloaded by any of the other electronic programmers 820B-820N communicatively coupled to it, assuming the user of these programmers has the right login permissions.

The database 900 may also include a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 900 is able to provide these functionalities at least in part via communication with the electronic programmer 820A and in response to the data sent by the electronic programmer 820A. These functionalities of the database 900 and its communications with the electronic programmer 820A will be discussed in greater detail later.

The medical infrastructure 800 further includes a manufacturer computer system 910. The manufacturer computer system 910 is also electronically or communicatively (for example through the Internet) coupled to the database 900. Hence, the manufacturer computer system 910 may also be considered a part of the cloud architecture. The computer system 910 is a computer system of medical device manufacturer, for example a manufacturer of the medical devices 810 and/or the electronic programmer 820A.

In various embodiments, the manufacturer computer system 910 may include one or more computer servers and/or client terminals that each includes the necessary computer hardware and software for conducting electronic communications and performing programmed tasks. In various embodiments, the manufacturer computer system 910 may include communications devices (e.g., transceivers), user input/output devices, memory storage devices, and computer processor devices that may share similar properties with the various components 830-870 of the electronic programmer 820A discussed above. Since both the manufacturer computer system 910 and the electronic programmer 820A are coupled to the database 900, the manufacturer computer system 910 and the electronic programmer 820A can conduct electronic communication with each other.

Figure 13:
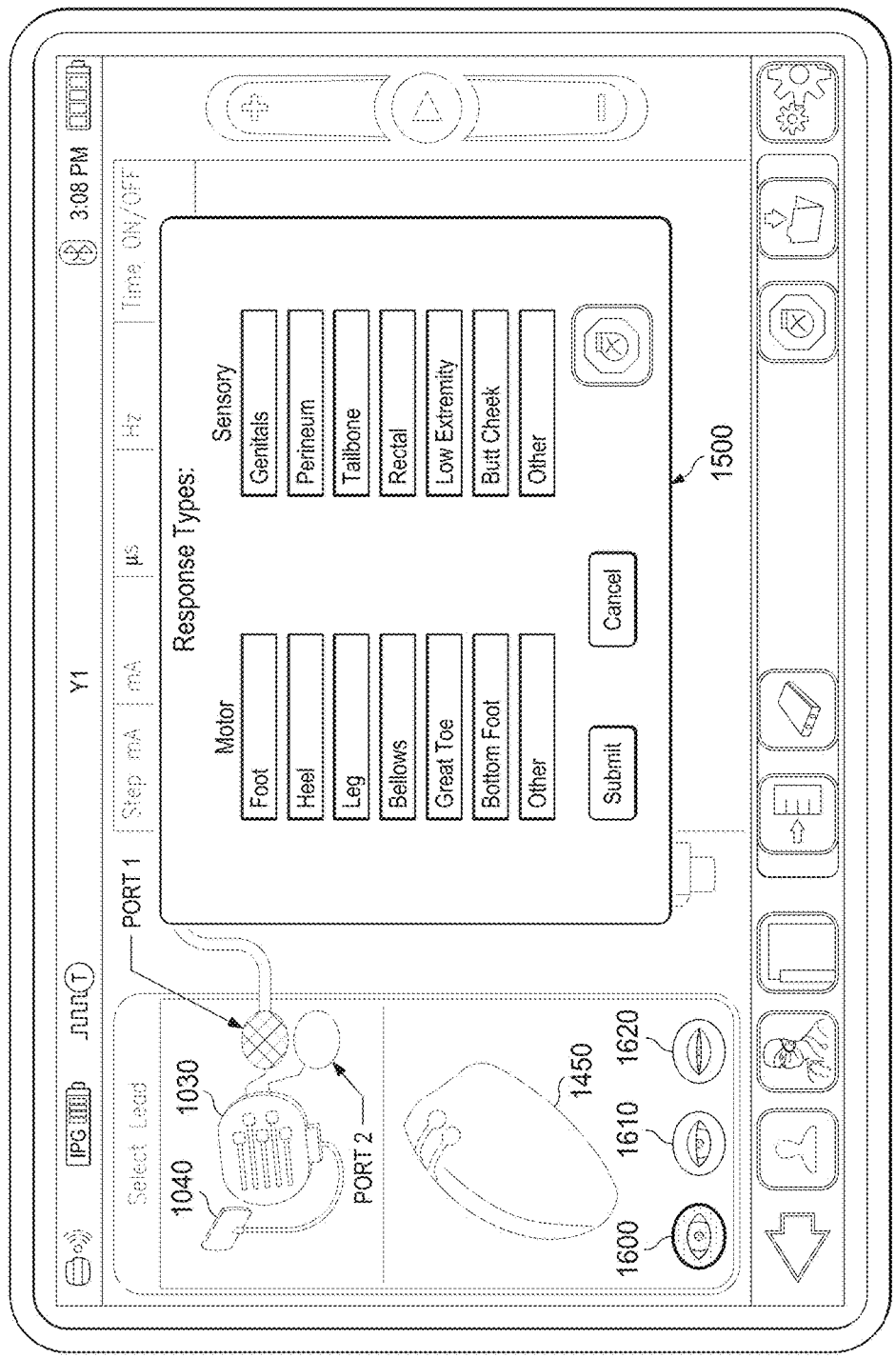
FIGS. 13-14 and 18-22 illustrate a graphical user interface of an electronic programmer according to various aspects of the present disclosure.

After an implantable lead (e.g., lead 10 discussed above with reference to FIGS. 2A-2B) has been placed inside the patient, an electronic programmer (e.g., the clinician programmer 22 discussed above with reference to FIG. 7) may be used to program a pulse generator (e.g., IPG 20 discussed above with reference to FIG. 8) to deliver electrical stimulation to the patient through the lead. For example, referring to FIGS. 13-14, the electronic programmer may provide a graphical user interface 1100 for programming the stimulation therapy and for recording the patient's responses to the stimulation therapy. In FIG. 13, the graphical user interface 1100 provides a menu 1500 that lists some common motor and sensory responses (collectively referred to as patient physiological responses) the patient may exhibit in response to the stimulation. The motor responses may include foot, heel, leg, bellows, great toe, bottom foot, and other (e.g., the user can input a custom response). The sensory responses may include genitals, perineum, tailbone, rectal, low extremity, butt cheek, and other (e.g., a custom response).

In addition to the responses being observed by the healthcare professional, a patient feedback mechanism 1450 (e.g., an embodiment of the patient feedback devices discussed above with reference to FIGS. 10A-10B and 11A-11C) may be used by the patient to communicate feedback of the stimulation to the healthcare professional. When appropriate, the healthcare professional may select one or more of these responses and press the "submit" button to record the particular manner the patient has responded to a given set of stimulation parameters and stimulation location. In another embodiment, the responses from the patient are recorded using an automatic closed-loop system using evoked potential sensors, for example as discussed in more detail in U.S. patent application Ser. No. 15/043,794, filed on Feb. 15, 2016, entitled "System and Method of Performing Computer Assisted Stimulation Programming (CASP) with a Non-Zero Starting Value Customized to a Patient" to Norbert et al., the contents of which are hereby incorporated by reference in its entirety.

Figure 14:
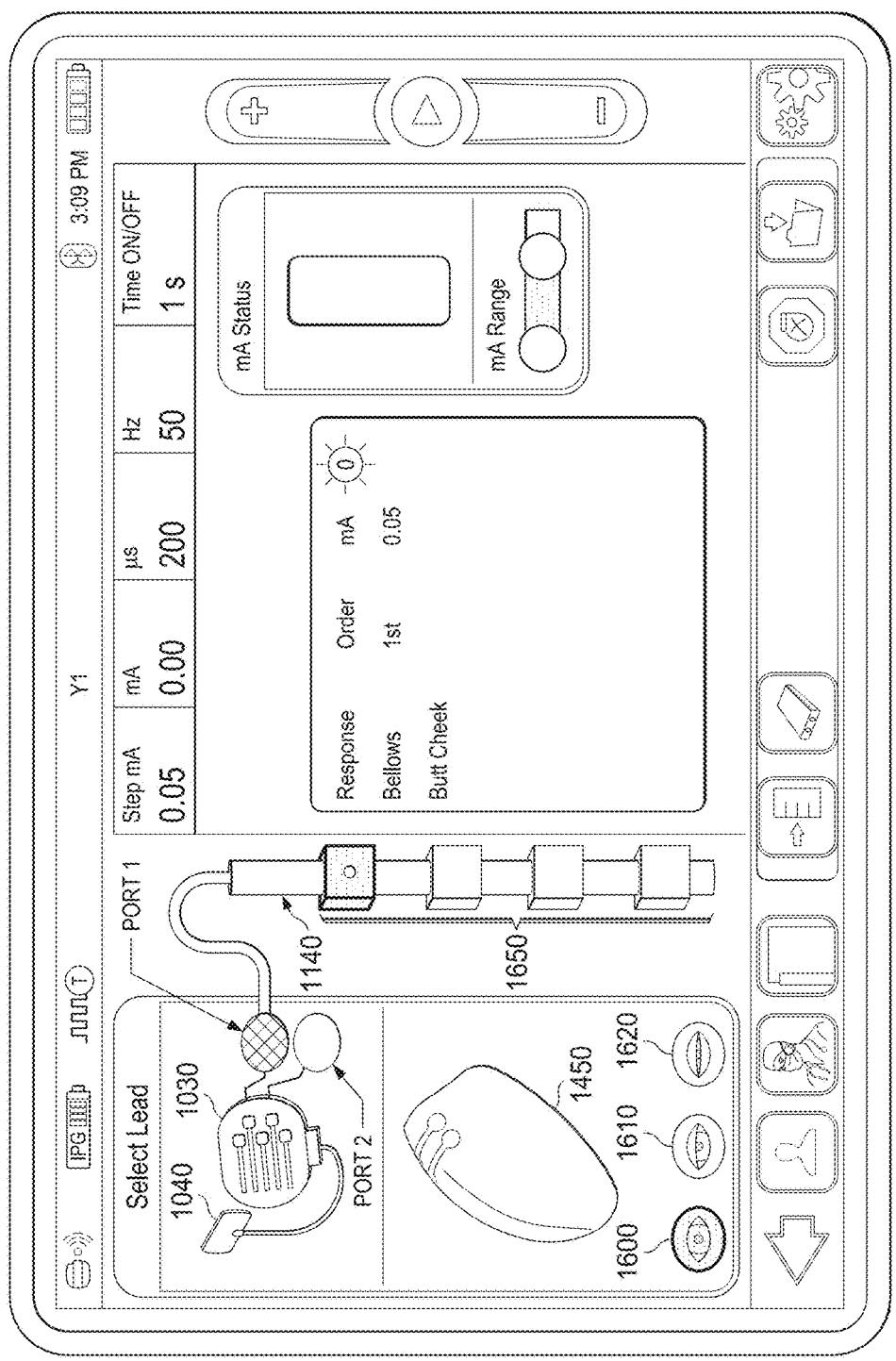

Still referring to FIGS. 13-14, the graphical user interface 1100 also displays a plurality of selectable buttons 1600-1620 to define the patient's current sedation state. As non-limiting examples, the button 1600 indicates that the patient is awake, another button 1610 indicates that the patient is sedated, and another button 1620 indicates that the patient is under general anesthesia. Each patient sedation state may have its own corresponding patient responses. In other words, the patient responses (and its associated stimulation parameters) may be recorded for each patient sedation state 1600/1610/1620. One of the reasons the sedation states are recorded in conjunction with patient responses is to determine whether the therapy has changed over time. The physician may compare current responses with those from the ones stored in the electronic programmer.

Referring to FIG. 14, the graphical user interface 1100 displays a virtual connection between a percutaneous lead 1140 with an external pulse generator (EPG) 1040 via a trial connector 1030. The graphical user interface 1100 in FIG. 14 also displays a plurality of selectable virtual contacts 1650 on the implantable percutaneous lead 1140. The contacts 1650 on the lead 1140 are separate and independent from one another. For example, the contacts 1650 are not shorted together, and each contact 1650 may be programmed with a different set of stimulation parameters like stimulation amplitude, frequency, pulse width, etc.

For each of these selected sedation states 1600/1610/1620, the healthcare professional may select one or more contacts 1650 and record the patient responses bellows or butt cheek) exhibited in association with that specific contact being activated to deliver the stimulation. In other words, each contact 1650 may have its own corresponding recorded patient physiological response, a set of stimulation parameters that resulted in the patient physiological response, and the patient's sedation state.

The efficacy of the pelvic or sacral nerve stimulation can be predicted or determined by observing the patient's physiological responses to the stimulation. In some embodiments, the stimulation is deemed effective only if the patient exhibits the following responses in the specified chronological order: an anal sphincter response, followed by a bellows response, which is then followed by a toes response. This is described in detail in U.S. patent application Ser. No. 15/043,954, filed on Feb. 15, 2016, and entitled "Systems, Methods, and Devices for Evaluating Lead. Placement Based on Patient Physiological Responses" to Norbert et al., the disclosure of which is hereby incorporated by reference it its entirety.

For the desired responses to occur according to the chronological order, the placement of the lead (e.g., the lead percutaneous 1140) inside the patient has to be optimal. In other words, the lead 1140 has to be implanted inside a correct target region of the patient's body in order for the pelvic or sacral nerve stimulation therapy to be effective. However, conventional pelvic or sacral nerve stimulation systems and methods do not provide a reliable and intuitive mechanism to inform the healthcare professional as to how well the lead 1140 has been implanted. Doctors may attempt to interpret medical images (e.g., fluoroscopies) regarding the lead implantation, and manually evaluate how well the lead has been implanted accordingly. However, interpreting medical images and determining lead placement requires a high level of skill, which some healthcare professionals do not possess due to lack of experience or training. Furthermore, even some experienced healthcare professionals do not know what to look for in a medical image. Consequently, lead placement evaluation has been difficult in conventional pelvic or sacral nerve stimulation.

To address this problem, the present disclosure generates visual representations of the sacrum and the lead based on a medical image (or medical scan), and evaluates the lead placement based on the generated visual representation of the sacrum and the lead, as discussed below.

Using the electronic programmer (such as a clinician programmer) of the present disclosure, or using a computer system, visual (e.g., 3D) representations of the sacrum and the lead based can be generated based on images obtained from sources such as fluoroscopies, CT scans, X-rays, ultrasounds etc. In some embodiments, fluoroscopy images from two planes are obtained—the AP plane (anterior posterior plane), which provides a top down view, and a lateral plane, which provides a side view.

Referring to g. 15, an example fluoroscopy image 1700A is illustrated. The fluoroscopy image 1700A illustrates the lateral plane. The bones of a sacrum 1720 are clearly shown in the fluoroscopy image 1700A. Also clearly shown in the fluoroscopy image 1700A is an implanted lead 1140. In this example, the implanted lead 1140 contains four contacts arranged in a row, though it is understood that other implantable leads having a different number (or arrangement) of contacts may be used in alternative embodiments.

Figure 15:
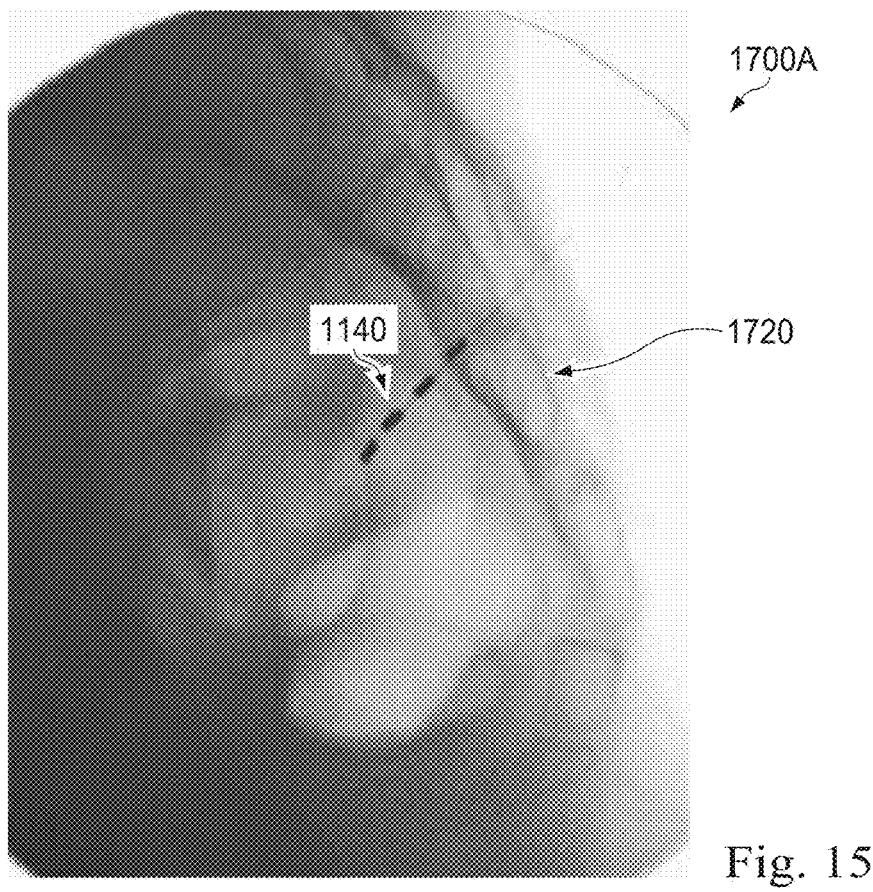
FIGS. 15-16 are example fluoroscopy according to various aspects of the present disclosure.
Figure 16:
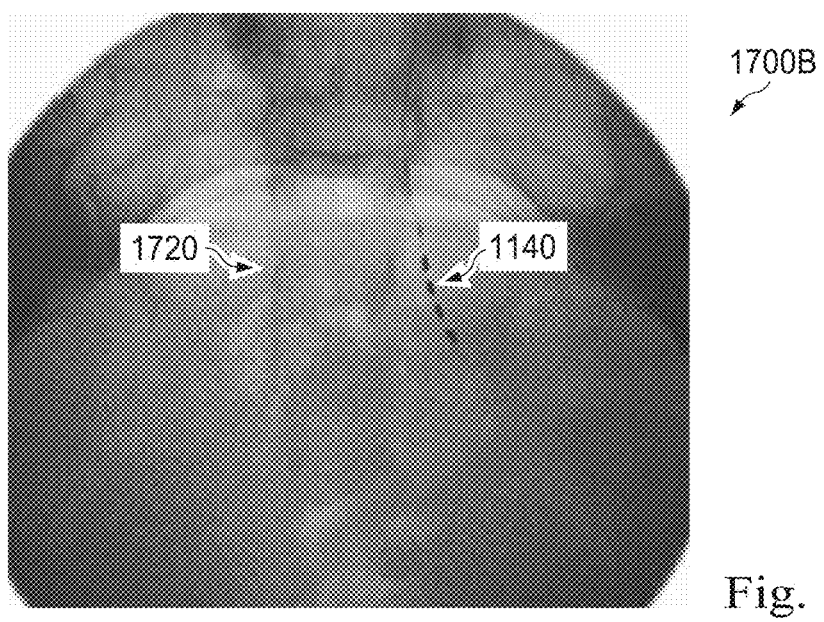

Referring to FIG. 16, an example fluoroscopy image 1700B is illustrated. The fluoroscopy image 1700B illustrates the AP plane. The bones of the sacrum 1720 as well as the implanted lead 1140 are also clearly shown in the fluoroscopy image 1700B, but in a different view from that shown in FIG. 15.

Based on the fluoroscopy images 1700A and 1700B, the individual contacts of the implanted lead 1140 are identified electronically. In an embodiment, a two-dimensional Fast Fourier Transform (FFT) is performed to each of the fluoroscopy images 1700A and 1700B. In general, Fourier transform converts a signal from its original domain (e.g., a time domain) to a representation in a frequency domain, or vice versa. An FFT rapidly computes such transformations by factorizing a Digital Fourier Transform (DFT) matrix into a product of sparse (mostly zero) factors. As a result, it manages to reduce the complexity of computing the DFT from $O(n^2)$, which arises if one simply applies the definition of DFT, to $O(n \log n)$, where a is the data size. Among other things, in the case of high pass filtering, the FFT process will detect the edges of the fluoroscopy images.

Thereafter, a high pass filtering process is executed to the fluoroscopy images to isolate the contacts. In other words, after the high pass filtering process is executed, the four contacts are what remain in the resulting high-pass-filtered images. A technique known as Component Labeling is then used to identify these contacts. For example, component labeling may be used to "group" pixels that share connected borders, either using a 4-pixel connectivity (up, down, right, left), or an 8-pixel (adding the diagonals) connectivity. The center of each of the contacts is identified, and the X coordinate and the Y coordinate for each center of the contact is therefore obtained.

The DFT, high pass filtering, and component labeling processes are performed for both the lateral plane fluoroscopy image 1700A and the AP plane fluoroscopy image 170N. When the X and Y coordinates are obtained for each of the contacts for both the lateral and AP planes, a curvature of the lead 1140 may be calculated. Based on the calculated curvature of the lead, a 3D model of the lead 1140 with respect to the sacrum 1720 may be constructed. In some embodiments, a sacrum plane may also be determined via similar processes.

Figure 17:
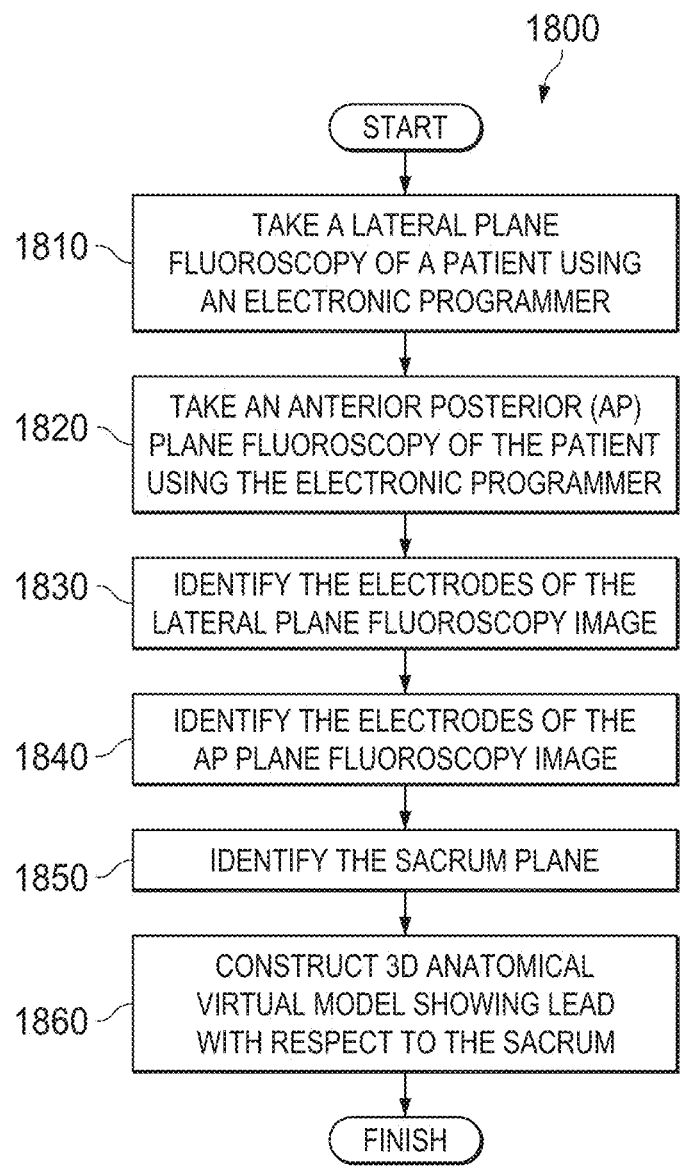
FIG. 17 is an example flowchart illustrating a method of constructing a 3D anatomical virtual model based on fluoroscopy images according to various aspects of the present disclosure.

FIG. 17 is a simplified flowchart illustrating a method 1800 of constructing a 3D virtual anatomical model based on fluoroscopy images. The method 1800 includes a step 1810, in which a lateral fluoroscopy image of a patient is taken using an electronic programmer. The patient has a lead implanted therein. The lead contains a plurality of electrode contacts. The electronic programmer may be the clinician programmer discussed above. The method 1800 includes a step 1820, in which an anterior posterior (AP) fluoroscopy image of the patient is taken using the electronic programmer. The method 1800 includes a step 1830, in which the electrodes of the implanted lead are identified for the lateral plane fluoroscopy image. The method 1800 includes a step 1840, in which the electrodes of the implanted lead are identified for the AP plane fluoroscopy image. The method 1800 includes a step 1850, in which the sacrum plane (in which the lead is implanted) is identified for the lateral plane image and the AP plane fluoroscopy image. The method 1800 includes a step 1860, in which a 3D anatomical virtual model is constructed. The 3D anatomical virtual model shows how the lead is implanted with respect to the sacrum. The curvature of the lead is also shown in the 3D virtual model, as well as the positions of the contacts of the lead with respect to the lead.

Figure 18:
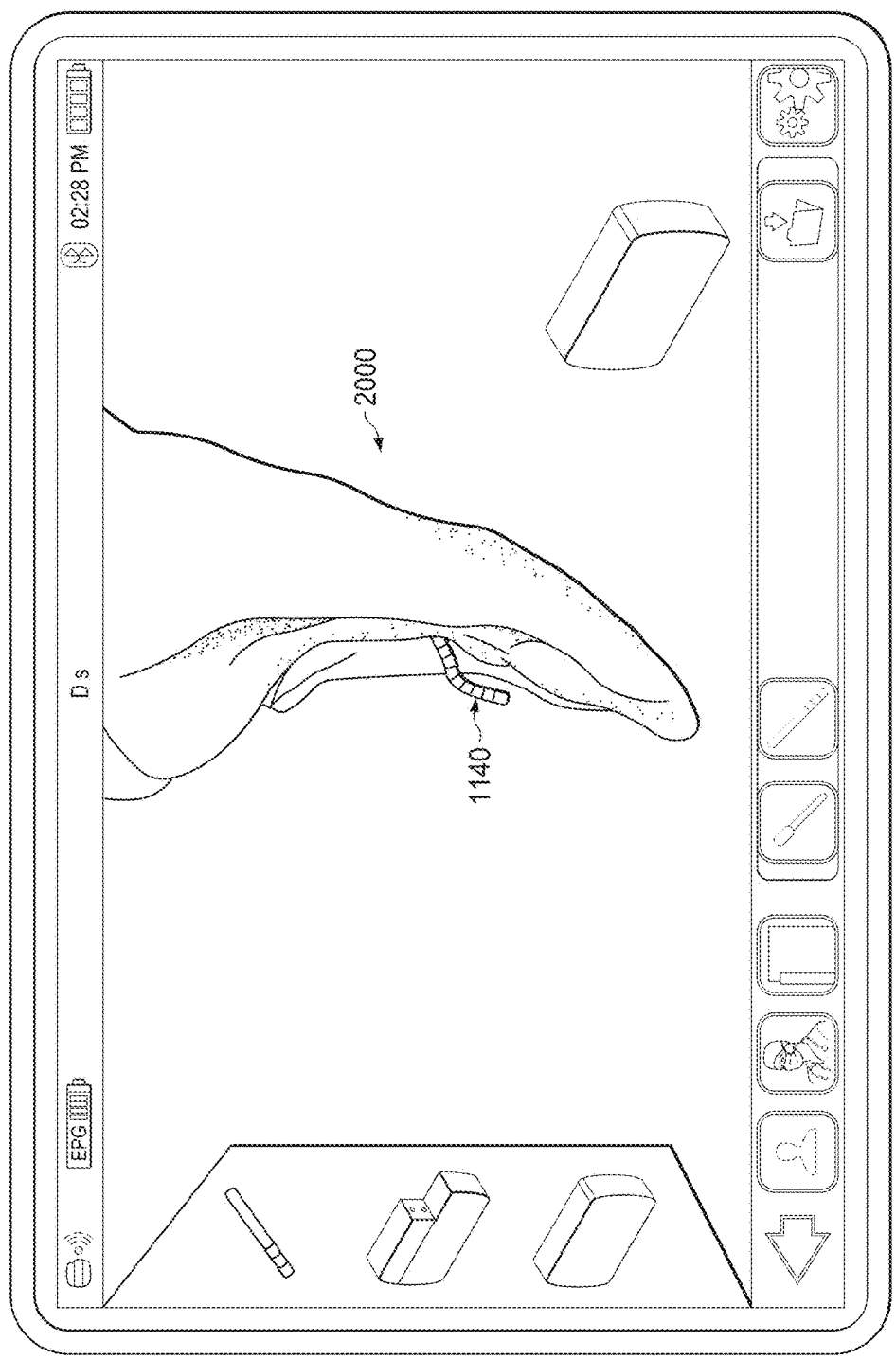
Figure 19:
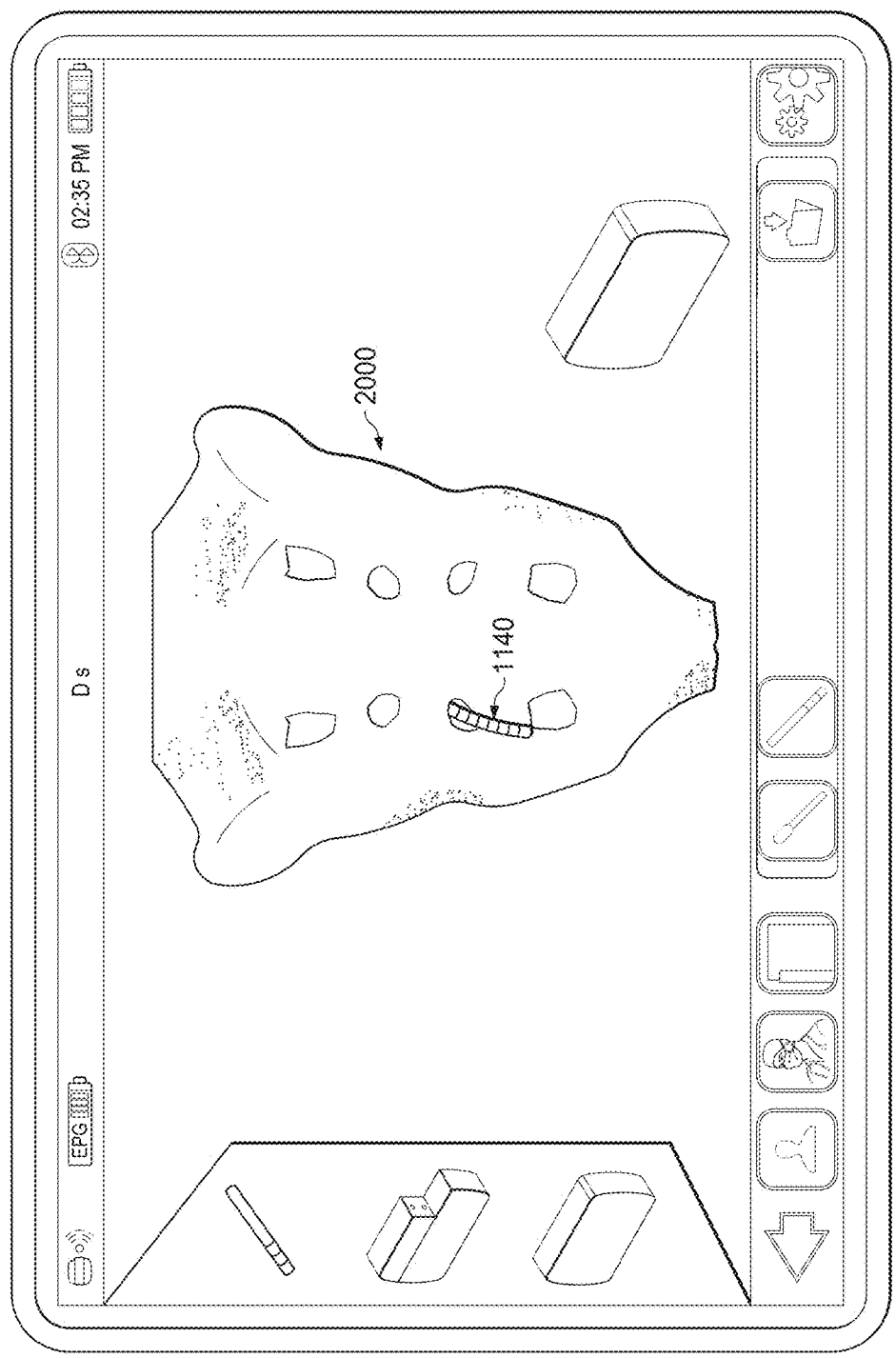

Based on the discussions above, it can be seen that the electronic programmer (e.g., the clinician programmer 22 discussed above with reference to FIG. 7) of the present disclosure is capable of generating 3-dimensional (3D) virtual models of the sacrum and the implanted lead 1140. These 3D virtual models are considered visual representations of the sacrum and the implanted lead 1140 and may be referred to interchangeably hereinafter. These visual representations may be illustrated via the graphical user interface 1100 of the electronic programmer, for example as shown in FIGS. 18-19. Specifically, the graphical user interface 110 in 18 displays the 3D virtual models of a sacrum 2000 and the implanted lead 1140 in a lateral view (or the lateral plane), and the graphical user interface 110 in FIG. 19 displays the 3D virtual models of the sacrum 2000 and the implanted lead 1140 in an anterior posterior (AP) view (or the AP plane). The 3D virtual models of the sacrum 2000 and the lead 1140 can be moved and rotated and otherwise manipulated through an interactive user engagement with the user interface 1100.

As discussed above, the disposition of the 3D virtual of the lead 1140 relative to the 3D virtual model of the sacrum 2000 is determined based on actual medical images or scans. As such, FIGS. 18-19 provide an accurate visual representation of how the lead 1140 is implanted inside the patient. Nevertheless, the electronic programmer herein also allows the healthcare professional to manually adjust these virtual models based on his experience of viewing and interpreting the source images (e.g., the fluoroscopy images) from which these 3D virtual models are constructed. For example, via the graphical user interface 1100, the healthcare professional may be able to resize (e.g., shrink or expand) the lead 1140, move the lead 1140 so that it is further in (or out) of a particular foramen in the sacrum 2000, move the lead 1140 so that one or more contacts on the lead 1140 are closer to (or farther away from) a specific region of the sacrum 2000, or bend the lead 1140 to adjust its curvature.

It is understood that, even without further adjustment by the user (e.g., the healthcare professional), the 3D virtual models 1140 and 2000 offer the user of the electronic programmer an visual illustration of how the lead 1140 is implanted with respect to the sacrum 2000 and how it is oriented. According to the various aspects of the present disclosure, how the lead 1140 is implanted and how it is bending (e.g., curvature) are important factors in the generation of effective sacral nerve stimulation therapy. In some embodiments, a successfully implanted lead 1140 should have the following characteristics (or meets the following tests):

1. The lead 1140 is implanted so that it is coming out of the S3 foramen of the sacrum 2000 and along a vertebral fusion plane. All of the lead contacts are supposed to be perturbing the pelvic bone.
2. The last contact on the lead 1140 (e.g., the fourth contact if it is a 4-contact lead) should be barely coming into (or out of) the pelvic floor (i.e., the bony edge of the sacrum 2000).
3. The lead 1140 should be bent (or curved) so that it follows a natural path of the sacral nerve. Note that the lead 1140 is not pre-bent before the implant procedure. It is the implant procedure itself under the guidance of a healthcare professional such as a surgeon—that results in the curvature of the lead 1140.

Each of the characteristics listed above may be considered a factor or a test, the satisfaction of which is an indication of how well the lead has been placed. If an implanted lead 1140 exhibits these above characteristics, there is a high likelihood that it will be able to deliver satisfactory sacral nerve stimulation therapy. For example, a successfully implanted lead is likely to evoke certain muscle contractions such as the anal sphincter contractions and the bellows and toes responses (in a desired chronological order in the sense that the stimulation amplitude is a dependent variable on time (e.g., increasing)). Therefore, based on the visual representation of the lead 1140 relative to the sacrum 2000 generated by the electronic programmer, the healthcare professional may quickly and accurately evaluate how well the lead 1140 has been implanted. If the lead placement is not satisfactory, which is evidenced by the 3D virtual model of the lead 1140 not meeting one or more of the criteria discussed above, then the healthcare professional may choose to reposition or adjust the actual implanted lead 1140 accordingly. Thereafter, updated medical images may be obtained for the patient (after the lead implant adjustment), and updated visual representations of the sacrum 2000 and the lead 1140 (i.e., revised 3D virtual models) may be generated again by the electronic programmer, and the healthcare professional may make an evaluation again on the adjusted lead placement. This process may be repeated until the healthcare professional is satisfied with the lead placement.

It is understood that the lead placement evaluation (based on the 3 factors discussed above) does not have to be performed by a human such as the healthcare professional. In some embodiments, the electronic programmer (using its hardware processors) automatically makes its own evaluation of the lead placement/implantation based on the visual representation of the sacrum 2000 and the lead 1140. This evaluation is also based on how well the three factors (regarding lead placement) discussed above has been met.

For the first factor (i.e., is the lead 1140 coming out of the S3 foramen along the vertebral fusion plane), the electronic programmer identifies the dark regions of the sacrum, where each of these darker regions of the sacrum corresponds to a respective foramen (e.g., S1, S2, S3, S4). Thus, the S3 foramen corresponds to the third darker region of the sacrum 2000 from the top. If the lead 1140 coincides with that, then the electronic programmer can automatically determine that the lead 1140 is inserted into the S3 foramen. This may be determined either using the digitally processed fluoroscopy images or by using the 3D virtual models.

Figure 20:
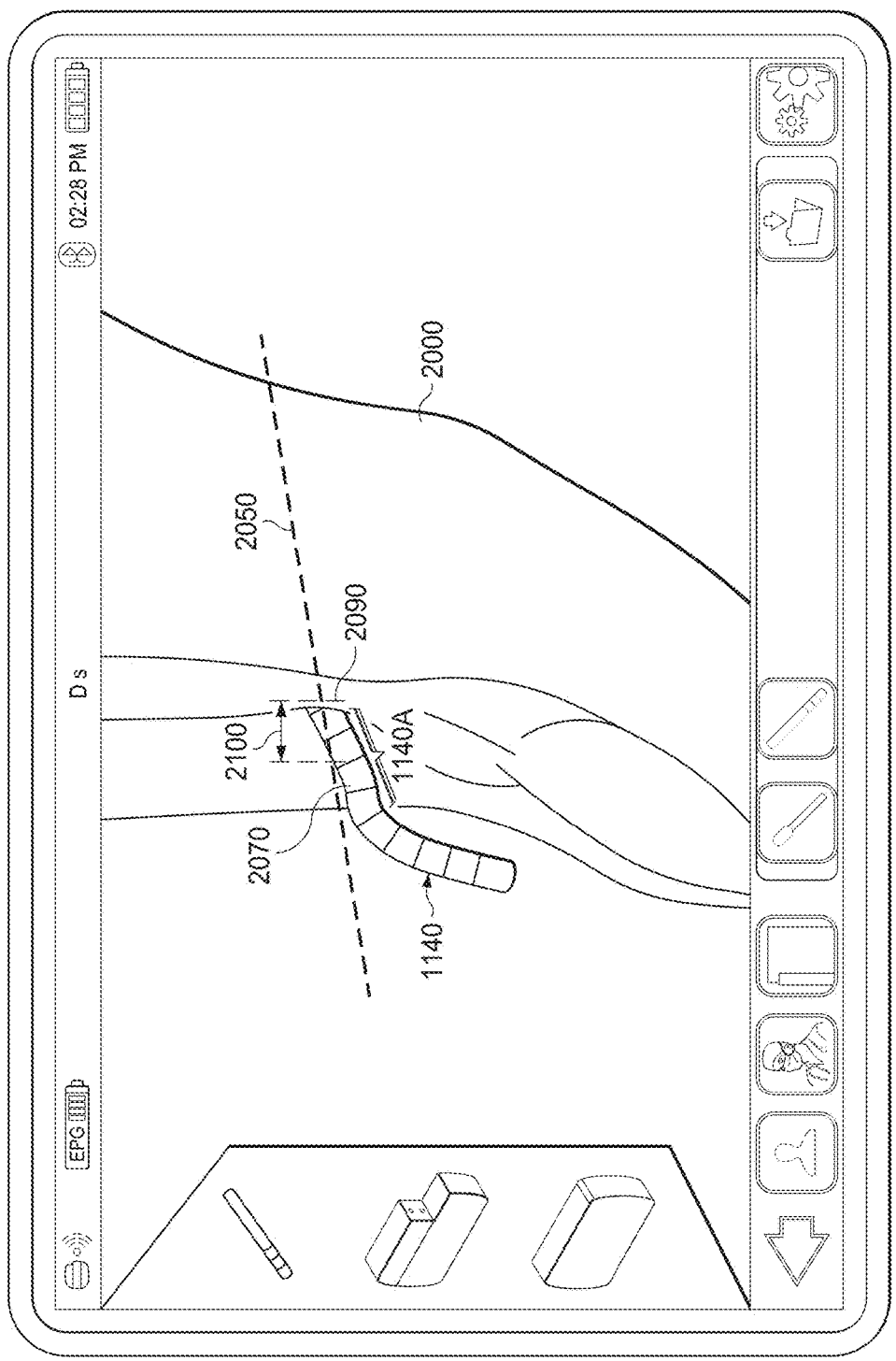

FIG. 20 illustrates a magnified portion of the visual representation of the sacrum 2000 and the lead 1140 to better illustrate the various aspects of the 3-factor test discussed above. For example, a vertebral fusion plane 2050 is illustrated as dashed lines in FIG. 20. The vertebral fusion plane 2050 roughly corresponds to a plane where the bones of the sacrum are fused together. The electronic programmer may calculate a trajectory of a segment 1140A of the lead that is coming out of the S3 foramen, and then determine whether that trajectory is consistent with the vertebral fusion plane 2050. For example, if the calculated trajectory is within plus/minus 20 degrees of the vertebral fusion plane 2050, then they are deemed sufficiently consistent, and the lead 1140 is deemed to be coming out of the S3 foramen, and along the vertebral fusion plane 2050. It is understood that the vertebral fusion plane 2050 may or may not be actually illustrated in the graphical user interface 1100, and it is shown in FIG. 20 merely for illustrative purposes.

For the second factor (is the 4th contact of the lead 1140 barely coming into (or out of) the pelvic floor?), the electronic programmer is configured to calculate a distance separating the last electrode contact (e.g., located at the end) of the lead 1140 from the honey edge of the sacrum 2000 nearby. In the illustrated embodiment, the last electrode contact of the lead 1140 is electrode contact 2070. The lead 1140 is a 4-contact lead (containing 4 electrode contacts), and thus the 4th contact 2070 is considered the last contact on the lead 1140. As shown in FIG. 20, a distance 2100 separates the 4th contact 2070 of the lead 1140 from the pelvic floor (e.g., the honey edge of the sacrum 2000).

In some embodiments, the value of the distance 2100 can be automatically calculated by the electronic programmer based on the dimensions of the lead 2000 or the contact 2070. For example, based on the visual representation of the lead 1140 and the sacrum 2000, the electronic programmer can capture one or more digital images, for example digital images similar to the one illustrated in FIG. 20. Digital image processing as discussed above may be performed for any one of the digital images, and the distance 2100 separating the 4th contact (or the last contact if the lead has more than 4 contacts) from the pelvic floor may be obtained, though the exact value of the distance 2100 is yet to be determined at this point.

Now, the actual dimensions of the lead 2000 and the contacts thereon are known because they are provided by the manufacturer. For the sake of discussion, suppose the length of the lead 1140 is X millimeters (mm), the width of the lead 1140 is Y mm, and the length of the contact 2070 is Z mm. The distance 2100 is compared to the dimensions of the lead 1140 or the dimension of the contact 2070. Since these dimensions are known, the value of the distance 2100 can now be calculated as a function of any of these dimensions. For example, if the length of the contact 2070 is Z mm, and the distance 2100 is measured to be approximately 1.5 times of the length of the contact 2070, then the distance 2100 is calculated to have a value of 1.5 Z mm. Similarly, if the length of the lead 1140 is X mm, and the distance 2100 is measured to be approximately 0.1 times of the length of the lead 1140, then the distance 2100 is calculated to have a value of 0.1 X mm.

In some embodiments, the electronic programmer will evaluate which of the dimensions (i.e., the length or width of the lead 1140, or the length or width of the contact 2070) is the easiest to measure based on the clarity of the captured digital image and/or based on the position of the lead 1140. The easier dimension to measure will then be used to derive the value of the distance 2100, since it likely provides the most accurate baseline value. In combination with (or separately from) this technique, the distance 2100 may also be calculated a plurality of times, and an average is obtained. For example, based on each of the processed images, the distance 2100 may be calculated a plurality of times, wherein each calculation is performed as a function of a different known lead or contact dimension. An average of these calculated distances 2100 may be a better representation of the actual value of the distance 2100. As another example, a calculated value of the distance 2100 (whether it is taken as a function of the easiest-measured dimension of the lead or contact, or as an average) may be obtained for each of a plurality of the captured digital images. These calculated values of the distance may then be averaged together to obtain a value of the distance 2100 that may be a more representative or accurate value of the actual distance between the last contact 2070 and the pelvic floor.

In other embodiments, the calculation of the value of the distance 2100 may involve manual input from the user. For example, the user may also user the graphical user interface 1100 to manually designate the distance 2100. For example, the user may click on a first point corresponding to the contact 2070 and then click on a second point corresponding to the pelvic floor, or vice versa. A distance between the first point and the second point is the distance 2100. Using a similar approach, the user may also manually measure one or more of the dimensions of the lead 1140 or the contact 2070. The value of the distance 2100 may then be calculated as a function of the dimensions of the lead 1140 or the contact 2070, since these dimensions are already known.

Regardless of how the distance 2100 is calculated, once it is calculated, it can be used as a way to determine whether the second factor discussed above is satisfied. For example, the second factor may be satisfied if the distance 2100 is less than (or within) a predetermined distance value. This predetermined distance value may be programmed into the electronic programmer by default, or it may be specified or changed by the user at any time, for example via a suitable user interaction with the user interface 1100. For example, if the predetermined distance is programmed to be 2 mm by default, or by user specification, and the distance 2100 is calculated to be 3 mm, then the second factor discussed above is not satisfied. However, if the distance is calculated to be 1 mm, then the second factor discussed above is considered satisfied.

For the third factor (the curvature of the lead), the electronic programmer is configured to determine the curvature in one of two ways, or a combination thereof. The first method is to take a plurality of sample points along the portion of the lead that is coming out of the foramen. For each of these sample points, a distance between it and a predetermined landmark (e.g., a particular region of the sacrum) is calculated, using techniques similar to those discussed above with the evaluation of the second factor. After these calculations have been performed, the electronic programmer can estimate the degree of curvature of the lead. This is because these distances discussed above will be different for a lead that is curved versus a lead that is straight, or a lead that is curved too much or not enough. Only a lead that is curved within a satisfactory range should yield the calculated distance values that match up with an expected range of values. A second method is to take a plurality of tangential segments along various portions of the lead that is coming out of the foramen. For each of these tangential segments, a rotation angle may be determined that indicates how bent a particular portion (the portion corresponding to the tangential segment) of the lead is. If these angles stay within a predetermined range, then the lead curvature is deemed to be satisfactory.

Figure 21:
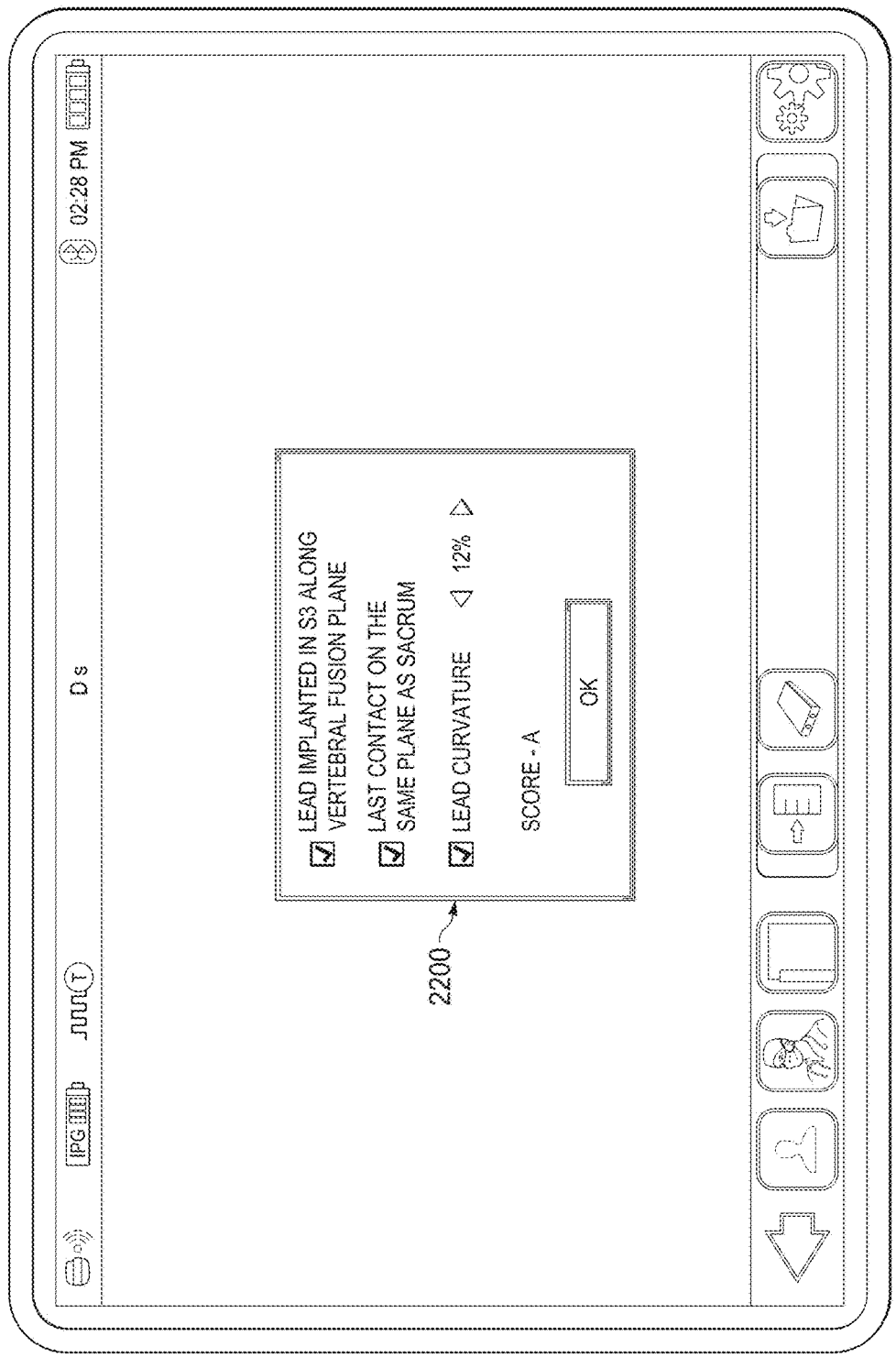

The electronic programmer may also communicate, to a user, how well the 3-factor test discussed above has been met. For example, referring to FIG. 21, the user interface 1100 may display a message box 2200 after the electronic programmer electronically evaluates (for example without human input) the satisfaction of each of the 3 factors discussed above. The message box 2200 contains the evaluation results. For instance, the message box 2200 may contain a short description of each of the 3 factors, such as "Lead implanted in S3 along the vertebral fusion plane", "Last contact on the same plane as sacrum", and "Lead curvature". A check-box is displayed next to each of the descriptions, and if the factor has been sufficiently satisfied, then a check mark is shown in the check-box (in this case, they have all been sufficiently satisfied). Additionally, the message box 2200 may display additional details, such as the degree of curvature of the lead (12% in this case) that has been determined by the electronic programmer. Lastly, the message box 2200 may compute a lead placement evaluation score, for example a score of "A" in this case (on a scale of A, B, C, D, and F). In other embodiments, the score may be a numeric score from 0 to 100.

Figure 22:
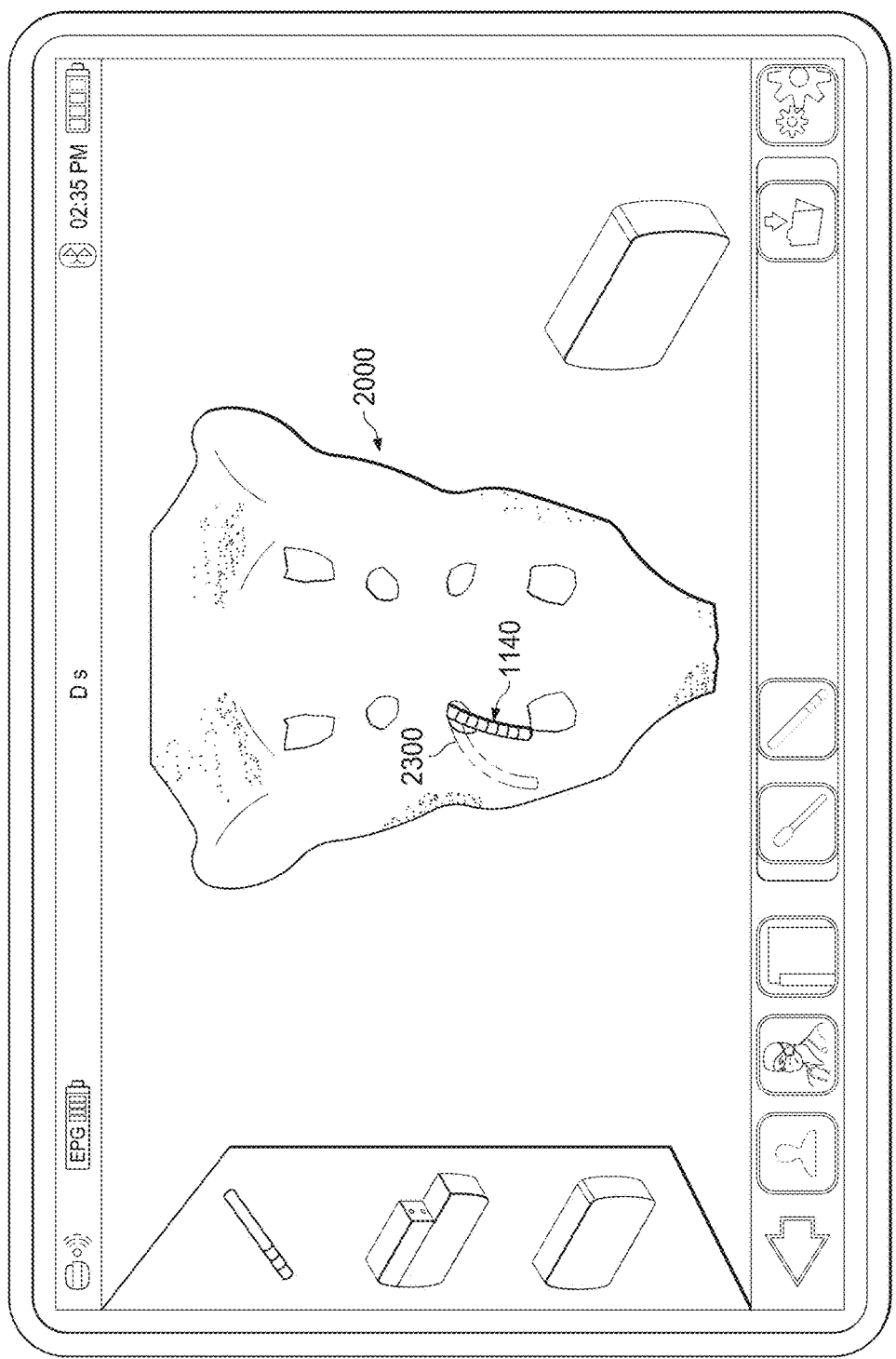

Referring now to FIG. 22, the electronic programmer may also display or superimpose an expected lead 2300 in the graphical user 1100 interface in some embodiments. For example, based on many successful lead implants, the electronic programmer may be able to determine an expected trajectory or path of a successfully implanted lead. In other words, if the actually implanted lead 1140 (or the virtual representation thereof based on fluoroscopy images) follows or matches up closely with the expected lead 2300, then the lead implant may be deemed successful. In some embodiments, the expected lead 2300 is generated based on an average of a plurality of locations of leads that have been implanted before. In other embodiments, the expected lead 2300 is generated based on calculations of the 3 factors discussed above. In any case, with this expect lead 2300 (or the path or trajectory thereof) displayed alongside superimposed on) the virtual model that represents the estimated position of the actually implanted lead, the healthcare professional may be above to see how well the lead has really been placed. Generally, the closer the estimated model of the lead 1140 matches up with the expected lead 2300, the better the lead placement is deemed to be.

In some embodiments, the electronic programmer may also be configured to communicate to the user as to how the lead should be adjusted or repositioned to achieve better efficacy. This may be based on the expected lead location. In the embodiment shown in FIG. 22, textual instructions may be displayed, such as "please reposition the lead toward the left of the patient." In other embodiments, audio or other visual graphical instructions (e.g., a short animation) may be used to communicate to the user as well. It is also understood that in some embodiments, the visual representation of the models may be used to determine lead migration, which may occur later on as the patient moves about.

Figure 23:
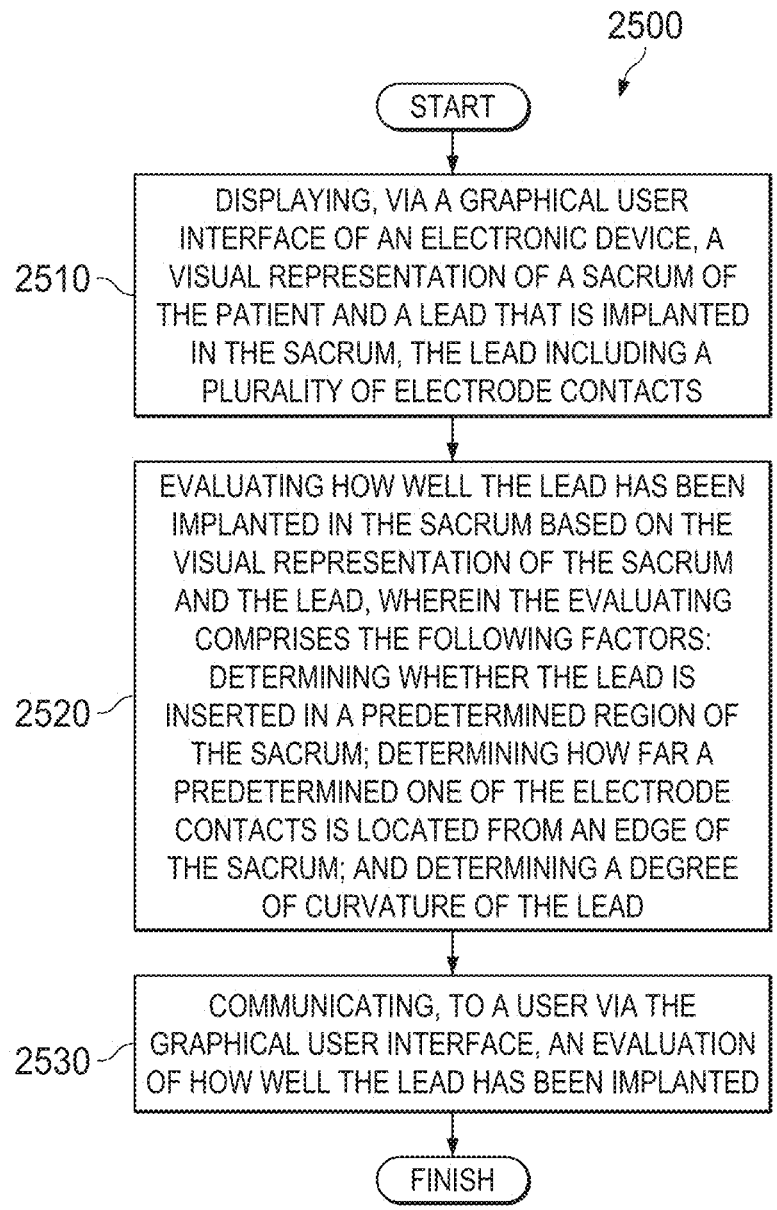
FIG. 23 is an example flowchart illustrating a method of evaluating lead placement according to various aspects of the present disclosure.

FIG. 23 is a flowchart illustrating a method 2500 of evaluating a placement of a lead configured to deliver an electrical stimulation therapy for a patient. In some embodiments, the steps of the method 2500 are performed by a portable electronic device, for example the clinician programmer discussed above with reference to FIGS. 2B and 7.

The method 2500 includes a step 2510 of displaying, via a graphical user interface of an electronic device, a visual representation of a sacrum of the patient and a lead that is implanted in the sacrum. The lead includes a plurality of electrode contacts. In some embodiments, the visual representation of the sacrum and the lead contains three-dimensional (3D) models. In some embodiments, the electronic device comprises a clinician programmer configured to program a pulse generator to deliver electrical stimulation to the patient through the lead.

The method 2500 includes a step 2510 of evaluating how well the lead has been implanted in the sacrum based on the visual representation of the sacrum and the lead. The evaluating comprises the following factors: determining whether the lead is inserted in a predetermined region of the sacrum; determining how far a predetermined one of the electrode contacts is located from an edge of the sacrum; and determining a degree of curvature of the lead. In some embodiments, the evaluating is performed automatically via one or more hardware processors of the electronic device. In some embodiments, the determining of whether the lead is inserted into a predetermined region of the sacrum comprises determining whether the lead is inserted into an S3 foramen and along a vertebral fusion plane. In some embodiments, the determining of how far the predetermined one of the electrode contacts is located from an edge of the sacrum comprises determining whether an electrode contact at an end of the lead is located within a predetermined distance from the edge of the sacrum. In some embodiments, the determining of the degree of curvature comprises determining whether the degree of curvature is within a predefined threshold.

The method 2500 includes a step 2530 of communicating, to a user via the graphical user interface, an evaluation of how well the lead has been implanted. In some embodiments, the communicating comprises providing, via the graphical user interface, instructions on guiding the user to reposition the lead.

It is understood that some of the steps 2510-2530 need not necessarily be performed sequentially unless otherwise specified. It is also understood that the method 2500 may include additional steps may be performed before, during, or after the steps 2510-2530. For example, the method 2500 may include a step of displaying, via the graphical user interface, a visual representation of an expected lead that is superimposed on the visual representation of the sacrum. The visual representation of the expected lead represents an implant location of the lead that is expected to result in optimal electrical stimulation therapy.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method of evaluating an implantation of a lead that is configured to deliver electrical stimulation to a patient, the method comprising:
   obtaining visual representations of a sacrum of the patient and the lead that is implanted in the sacrum; and
   evaluating a placement of the lead by analyzing the visual representations of the sacrum and the lead to determine whether one or more of the following factors are met:
   a first factor involving which foramen of the sacrum the lead is implanted in;
   a second factor involving how far the lead is coming out of a pelvic floor of the patient; or
   a third factor involving how bent the lead is.

2. The method of claim 1, wherein the first factor is met if the lead is implanted in an S3 foramen of the sacrum.

3. The method of claim 1, wherein the second factor is met if a last contact of the lead is located proximate to the pelvic floor.

4. The method of claim 1, wherein the third factor is met if a curvature of the lead conforms to a predetermined curvature range.

5. The method of claim 1, further comprising: communicating a result of the evaluating to a user.

6. The method of claim 1, wherein the obtaining comprises:
   receiving one or more fluoroscopy images of the patient; and
   constructing the visual representations by digitally processing the one or more fluoroscopy images.

7. The method of claim 6, wherein the constructing comprises digitally processing a lateral fluoroscopy image of the patient and an anterior posterior fluoroscopy image of the patient.

8. An electronic device, comprising:
   an electronic memory storage configured to store programming instructions; and
   one or more processors configured to execute the programming instructions to perform operations that include:
   obtaining visual representations of a sacrum of a patient and a lead that is implanted in the sacrum; and
   evaluating a placement of the lead by analyzing the visual representations of the sacrum and the lead to determine whether one or more of the following factors are met:
   a first factor involving which foramen of the sacrum the lead is implanted in;

a second factor involving how far the lead is coming out of a pelvic floor of the patient; or a third factor involving how bent the lead is.

9. The electronic device of claim 8, wherein the first factor is met if the lead is implanted in an S3 foramen of the sacrum.

10. The electronic device of claim 8, wherein the second factor is met if a last contact of the lead is located proximate to the pelvic floor.

11. The electronic device of claim 8, wherein the third factor is met if a curvature of the lead conforms to a predetermined curvature range.

12. The electronic device of claim 8, further comprising a user interface, and wherein the operations further includes:

displaying the visual representations of the sacrum and the lead; and communicating a result of the evaluating to a user.

13. The electronic device of claim 8, wherein the obtaining comprises:

receiving one or more fluoroscopy images of the patient; and constructing the visual representations by digitally processing the one or more fluoroscopy images.

14. The electronic device of claim 13, wherein the constructing comprises digitally processing a lateral fluoroscopy image of the patient and an anterior posterior fluoroscopy image of the patient.

15. A medical system, comprising:

a pulse generator configured to generate electrical stimulation pulses as a part of an electrical stimulation therapy for a patient;

a lead configured to be implanted inside the patient to deliver the electrical stimulation pulses to the patient; and an electronic programming device that is configured to conduct electronic communications with the pulse generator, wherein the electronic programming device is configured to perform operations that include:

obtaining visual representations of a sacrum of a patient and the lead that is implanted in the sacrum; and evaluating a placement of the lead by analyzing the visual representations of the sacrum and the lead to determine whether one or more of the following factors are met:

a first factor involving which foramen of the sacrum the lead is implanted in;

a second factor involving how far the lead is coming out of a pelvic floor of the patient; or a third factor involving how bent the lead is.

16. The medical system of 15, wherein the first factor is met if the lead is implanted in an S3 foramen of the sacrum.

17. The medical system of 15, wherein the second factor is met if a last contact of the lead is located proximate to the pelvic floor.

18. The medical system of 15, wherein the third factor is met if a curvature of the lead conforms to a predetermined curvature range.

19. The medical system of 15, wherein the obtaining comprises:

receiving one or more fluoroscopy images of the patient; and constructing the visual representations by digitally processing the one or more fluoroscopy images.

20. The medical system of 19, wherein the constructing comprises digitally processing a lateral fluoroscopy image of the patient and an anterior posterior fluoroscopy image of the patient.

* * * * *